US011918287B2

(12) United States Patent
Yehezkel et al.

(10) Patent No.: US 11,918,287 B2
(45) Date of Patent: Mar. 5, 2024

(54) METHOD AND DEVICE FOR TREATING / PREVENTING REFRACTIVE ERRORS AS WELL AS FOR IMAGE PROCESSING AND DISPLAY

(71) Applicant: NovaSight Ltd., Airport City (IL)

(72) Inventors: Oren Yehezkel, Ramat Gan (IL); Dan Oz, Even Yehuda (IL); Ran Yam, Jerusalem (IL)

(73) Assignee: NovaSight Ltd. (IL)

( * ) Notice: Subject to any disclaimer, the term of this patent is extended or adjusted under 35 U.S.C. 154(b) by 0 days.

(21) Appl. No.: 17/863,715

(22) Filed: Jul. 13, 2022

(65) Prior Publication Data

US 2023/0200639 A1 Jun. 29, 2023

Related U.S. Application Data

(60) Provisional application No. 63/293,909, filed on Dec. 27, 2021.

(51) Int. Cl.
*A61B 3/02* (2006.01)
*A61B 3/00* (2006.01)
*A61B 3/028* (2006.01)
*A61B 3/10* (2006.01)
*A61B 3/113* (2006.01)
*A61B 3/14* (2006.01)

(52) U.S. Cl.
CPC ............ *A61B 3/028* (2013.01); *A61B 3/0041* (2013.01); *A61B 3/113* (2013.01); *A61B 3/145* (2013.01)

(58) Field of Classification Search
CPC ......... A61B 3/02; A61B 3/102; A61B 3/1025; A61B 3/113; A61B 3/1015; A61B 3/103; A61B 3/1225; A61B 3/032; A61B 3/005

USPC ........ 351/222, 200, 205, 206, 209–211, 221, 351/239–244, 246
See application file for complete search history.

(56) References Cited

U.S. PATENT DOCUMENTS

| | | | |
|---|---|---|---|
| 7,832,859 B2 | 11/2010 | Phillips | |
| 8,899,746 B2 | 12/2014 | Back | |
| 9,952,434 B2* | 4/2018 | Jiao | G02B 27/0081 |
| 11,064,882 B2 | 7/2021 | Oz et al. | |
| 2002/0176113 A1* | 11/2002 | Edgar | H04N 1/4092 |
| | | | 382/266 |
| 2012/0113386 A1 | 5/2012 | Back | |
| 2018/0096461 A1* | 4/2018 | Okayama | G06V 40/174 |
| 2018/0168444 A1 | 6/2018 | Foss | |
| 2019/0094552 A1* | 3/2019 | Shousha | G02B 27/0179 |
| 2019/0246889 A1 | 8/2019 | Marin et al. | |

(Continued)

FOREIGN PATENT DOCUMENTS

WO 2021/205323 A1 10/2021

OTHER PUBLICATIONS

Read et al., "Light Exposure and Eye Growth in Childhood", Investigative Ophthamology & Visual Science, Oct. 2015, vol. 56, No. 11, pp. 6779-6787, retrieved from https://iovs.arvojournals.org/ on Sep. 13, 2018.

*Primary Examiner* — Dawayne Pinkney
(74) *Attorney, Agent, or Firm* — Endurance Law Group PLC; James R. Yee

(57) ABSTRACT

Disclosed are methods and devices useful in the field of image processing and display Disclosed are also methods and devices useful in the field of ophthalmology and, in some particular embodiments, useful for the non-invasive treatment and/or prevention of refractive errors.

30 Claims, 10 Drawing Sheets

(56) References Cited

U.S. PATENT DOCUMENTS

| | | | |
|---|---|---|---|
| 2019/0377191 A1* | 12/2019 | Hughes | G02B 27/0176 |
| 2021/0112226 A1 | 4/2021 | Abou Shousha | |
| 2022/0057651 A1* | 2/2022 | Segre | G02C 7/102 |
| 2022/0319708 A1* | 10/2022 | Hart | G16H 50/20 |

* cited by examiner

METHOD AND DEVICE FOR TREATING / PREVENTING REFRACTIVE ERRORS AS WELL AS FOR IMAGE PROCESSING AND DISPLAY

CROSS REFERENCE TO RELATED APPLICATIONS

This application claims priority to United Provisional Patent Application Ser. No. U.S. 63/293,909 filed on Dec. 27, 2021, the entire disclosure of which is hereby incorporated by reference and relied upon.

FIELD AND BACKGROUND OF THE INVENTION

The invention, in some embodiments, relates to the field of image processing and display, and, more particularly but not exclusively, to methods and devices useful for image processing and display of such images to a human subject. The invention, in some embodiments, relates to the field of ophthalmology and, more particularly but not exclusively, to methods and devices useful for non-invasive treatment and/or prevention of refractive errors in a human subject.

The eye of a full-term human baby is about 1.8 cm long (cornea to back of the eye). The eye grows throughout childhood, reaching a length of about 2.5 cm in adulthood during which, ideally, emmetropization occurs.

Emmetropia is a match between the power of the optics of the eye and the axial length of the eye so that in the absence of accommodation, distant images are focused at the photoreceptor layer.

Emmetropization is the process of achieving emmetropia and involves a reduction in the refractive error that is present at birth. The refractive state of a newborn human varies between individuals, most newborn's eyes being hyperopic and over time usually becoming emmetropic. The ocular components of the eye, notably the lens and the corneal curvature, continue to change and eye growth occurs beyond the time that initial emmetropia is obtained. Thus the eye also needs to maintain emmetropia. It is undisputed that emmetropization is in part actively achieved through visual feedback. Less is known about the processes underlying the maintenance of emmetropia.

In some instances, the eye reaches emmetropia but continues physically changing, eventually developing myopia. Such myopia is usually caused by an increase in eye axial-length and/or corneal curvature so that light from distant objects is focused in front of the retina leading to reduced visual acuity.

Myopia, also known as nearsightedness, is the most common eye disorders in the world. The prevalence of myopia is about 30 to 40 percent among adults in Europe and the United States, and up to 80 percent or higher in the Asian youth, especially in China. Some children who develop myopia have a continual progression of their myopia throughout the school years, including high school. Long-term risks associated with myopia progression include cataracts, glaucoma, macular degeneration and retinal detachment.

In U.S. Pat. No. 11,064,882 of the Applicant, is described an apparatus for screening, monitoring and/or assessment of visual impairments.

SUMMARY OF THE INVENTION

Some embodiments, relates to the field of image processing and display, and, more particularly but not exclusively, to methods and devices useful for image processing and display of such images to a human subject. Some embodiments of the invention herein relate to methods and devices useful in the field of ophthalmology and, in some particular embodiments, useful for the non-invasive treatment and/or prevention of refractive errors, particularly myopia. Some embodiments of the teachings herein are useful for one or more of: preventing the development of refractive errors, stopping the progression of extant refractive errors and reducing the severity of extant refractive errors, particularly myopia, hyperopia and astigmatism.

According to an aspect of some embodiments of the teachings herein, there is provided a method useful for the treatment of existing refractive errors and/or prevention of the development of refractive errors in a human subject, comprising:

a. determining a gaze direction of a first eye of a subject viewing an image on a display screen and providing the determined gaze direction to a computer processor;

b. subsequent to 'a', based on the determined gaze direction of the first eye, with a computer processor generating a display image for display to the first eye on the display screen from a received digital base image, wherein:

i. a central-vision portion of the display image that corresponds to a portion of the field of view of the first eye that includes the determined gaze direction is either:
unmodified compared to a corresponding portion in the base image; or
modified so that visual characteristics of the central-vision portion of the display image are changed compared to corresponding visual characteristics of a corresponding portion in the base image which modification improves the image quality of the central-vision portion relative to the corresponding portion in the base image, and ii. a non-central vision portion of the display image that is different from the central-vision portion is either:
unmodified compared to a corresponding portion in the base image; or
modified so that visual characteristics of the non-central vision portion of the display image are changed compared to corresponding visual characteristics of a corresponding portion in the base image, wherein as a result of the generating, an image quality of the non-central vision portion of the display image is lower than the image quality of the central-vision portion of the display image; and c. displaying the generated display image on the display screen so that the first eye of the subject views the display image on the display screen.

According to an aspect of some embodiments of the teachings herein, there is also provided a method for image processing and display, comprising:

a. determining a gaze direction of a first eye of a person viewing an image on a display screen and providing the determined gaze direction to a computer processor;

b. subsequent to 'a', based on the determined gaze direction of the first eye, with a computer processor generating a display image for display to the first eye on the display screen from a received digital base image, wherein:

i. a central-vision portion of the display image that corresponds to a portion of the field of view of the first eye that includes the determined gaze direction is either:

unmodified compared to a corresponding portion in the base image; or modified so that visual characteristics of the central-vision portion of the display image are changed compared to corresponding visual characteristics of a corresponding portion in the base image which modification improves the image quality of the central-vision portion relative to the corresponding portion in the base image, and ii. a non-central vision portion of the display image that is different from the central-vision portion is either:

unmodified compared to a corresponding portion in the base image; or modified so that visual characteristics of the non-central vision portion of the display image are changed compared to corresponding visual characteristics of a corresponding portion in the base image, wherein as a result of the generating, the image quality of the non-central vision portion of the display image is lower than the image quality of the central-vision portion of the display image; and c. displaying the generated display image on the display screen so that the first eye of the person views the display image on the display screen.

In some embodiments, either method further comprises displaying the generated display image on a display screen so that the second eye of the subject views the display image on a display screen (i.e., the same display screen or a different display screen). In some such embodiments, the display image is displayed at a same location of the display screen for both eyes to view simultaneously.

Alternatively, in some embodiments either method further comprises, concurrently with 'a' and 'b':

d. determining a gaze direction of a second eye of the subject (person) viewing a second eye display screen and providing the determined gaze direction to a computer processor;

e. subsequent to 'c', based on the determined gaze direction of the second eye, with a computer processor generating a second display image for display to the second eye on the second eye display screen from the received digital base image, wherein:

i. a central-vision portion of the second display image that corresponds to a portion of the field of view of the second eye that includes the determined gaze direction is either:

unmodified compared to a corresponding portion in the base image; or modified so that visual characteristics of the central-vision portion of the second display image are changed compared to corresponding visual characteristics of a corresponding portion in the base image which modification improves the image quality of the central-vision portion relative to the corresponding portion in the base image, and ii. a non-central vision portion of the second display image that is different from the central-vision portion is either:

unmodified compared to a corresponding portion in the base image; or modified so that visual characteristics of the non-central vision portion of the second display image are changed compared to corresponding visual characteristics of a corresponding portion in the base image, wherein as a result of the generating, the image quality of the non-central vision portion of the second display image is lower than the image quality of the central-vision portion of the second display image; and f. displaying the generated second display image on the second eye display screen so that the second eye of the subject (person) views the second display image on the second eye display screen.

In such embodiments, the displaying is such that the second eye does not see the display image, and the first eye does not see the second display image. In some such embodiments, the second eye display screen and the display screen are two different physical components (e.g., some VR glasses). In some such embodiments, the second eye display screen and the display screen are the same physical screen, but the second display image and the display image are displayed on different locations of the screen (e.g., some VR glasses with a left eye/right eye partition), are displayed at the same place of the screen but at different times (e.g., shutter glasses) or are displayed at the same place at the same time on the same screen (e.g., using anaglyph or autostereoscopic methods).

In some embodiments, the central-vision portion of the display image corresponds to a field of view of the first eye that is centered around the determined gaze direction of the first eye. Similarly, when applicable, in some embodiments the central-vision portion of the second display image corresponds to a field of view of the second eye that is centered around the determined gaze direction of the second eye.

In some embodiments, the shape of the central-vision portion of the display image is a circle. Similarly, when applicable, in some embodiments, the shape of the central-vision portion of the second display image is a circle.

In some embodiments, the size of the central-vision portion of the display image corresponds to a field of view of the first eye of at least about 1° and not more than about 20° (and, in particularly preferred embodiments, not less than about 2° and not more than about 8°) that includes the determined gaze direction of the first eye. Similarly, when applicable, in some embodiments the size of the central-vision portion of the second display image corresponds to a field of view of the second eye of at least about 1° and not more than about 20° (and, in particularly preferred embodiments, not less than about 2° and not more than about 8°) that includes the determined gaze direction of the second eye.

In some embodiments, the central-vision portion of the display image is unmodified compared to a corresponding portion in the base image. Similarly, when applicable, in some the central-vision portion of the second display image is unmodified compared to a corresponding portion in the base image.

Alternatively, in some embodiments the central-vision portion of the display image is modified so that visual characteristics of the central-vision portion of the display image are changed compared to corresponding visual characteristics of a corresponding portion in the base image which modification changes the image quality of the central-vision portion relative to the corresponding portion in the base image. In some embodiments, such modification improves the image quality of the central-vision portion of the display image relative to the corresponding portion in the base image. Similarly, in some embodiments the central-vision portion of the second display image is modified so that visual characteristics of the central-vision portion of the display image are changed compared to corresponding visual characteristics of a corresponding portion in the base image which modification changes the image quality of the central-vision portion relative to the corresponding portion in the base image. In some embodiments, such modification improves the image quality of the central-vision portion of the second display image relative to the corresponding portion in the base image.

The relative orientation of the central vision portion and the non-central vision portion in the display image and/or second display image is any suitable relative orientation. In some embodiments, the non-central vision portion is contiguous with the central vision portion. In some embodiments, the non-central vision portion of the display image at least partially surrounds the central vision portion. In some embodiments, the non-central vision portion of the display image completely surrounds the central-vision portion.

In some embodiments, the radial dimensions of the non-central vision portion of the display image corresponds to a field of view of the first eye of at least about 2°. Similarly and when applicable, in some embodiments the radial dimensions of the non-central vision portion of the second display image corresponds to a field of view of the first eye of at least about 2°.

In some embodiments, the non-central vision portion is at least 1% of the area of the display image that is not the central-vision portion. Similarly and when applicable, in some embodiments, the non-central vision portion is at least 1% of the area of the second display image that is not the central-vision portion. In some preferred embodiments, the non-central vision portion of the display image and/or the second display image is at least about 30% of the area of the display image that is not the central-vision portion. In some preferred embodiments, the non-central vision portion of the display image and/or the second display image is at least about 40%, at least about 50%, at least about 60%, at least about 70% at least about 80%, at least about 90%, at least about 95% and even about 100% area of the display image/second display image that is not the central-vision portion.

In some embodiments, the non-central vision portion of the display image is unmodified compared to a corresponding portion in the base image. Similarly, when applicable, in some the non-central vision portion of the second display image is unmodified compared to a corresponding portion in the base image.

In some preferred embodiments the non-central vision portion of the display image is modified so that visual characteristics of the non-central vision portion of the display image are changed compared to corresponding visual characteristics of a corresponding portion in the base image which modification changes the image quality of the non-central vision portion of the display image relative to the corresponding portion in the base image. In some embodiments, such modification improves the image quality of the non-central vision portion of the display image relative to the corresponding portion in the base image. In some preferred embodiments, such modification degrades the image quality of the non-central vision portion of the display image relative to the corresponding portion in the base image. Similarly, when applicable, in some preferred embodiments the non-central vision portion of the second display image is modified so that visual characteristics of the non-central vision portion of the second display image are changed compared to corresponding visual characteristics of a corresponding portion in the base image which modification changes the image quality of the non-central vision portion of the second display image relative to the corresponding portion in the base image. In some embodiments, such modification improves the image quality of the non-central vision portion of the second display image relative to the corresponding portion in the base image. In some embodiments, the modification which degrades the image quality of the non-central vision portion of the display image and/or the second display image relative to the corresponding portion in the base image includes at least one member selected from the group consisting of: reduced resolution; blurring; reduced contrast; reduced/increased brightness; reduced color intensity; reduced or changed color palette and combinations thereof. In preferred embodiments, the modification which degrades the image quality of the non-central vision portion of the display image and/or the second display image relative to the corresponding portion in the base image includes at least one member selected from the group consisting of: reduced resolution; blurring; reduced contrast and combinations thereof.

In some embodiments, the generating of a display image comprises generating the display image as an image data structure which is the outcome of running a graphical operator over the base image data structure and the displaying of the generated display image is subsequently displaying of the image data structure on the display screen. Similarly and when applicable, in some embodiments the generating of a second display image comprises generating the second display image as an image data structure and the displaying of the generated second display image is subsequently displaying of the image data structure on the display screen.

Alternatively, in some embodiments, the generating of a display image comprises generating a mask image which is non dependent on the base image, comprising a non-degrading central vision portion and a degrading non-central vision portion; and subsequently displaying the generated mask image together with the base image on the display screen so as to generate and display the display image. Similarly and when applicable, in some embodiments, the generating of a second display image comprises generating a second mask image comprising a non-degrading central vision portion and a degrading non-central vision portion; and subsequently displaying the generated second mask image together with the base image on the display screen so as to generate and display the second display image.

In some embodiments, the method further comprises: prior to the generating a display image 'b', providing the computer processor with a display screen to first-eye cornea distance; and the generating of the display image is also based on the provided display screen to first-eye cornea distance. Similarly, when applicable, in some embodiments, the method further comprises: prior to the generating a second display image 'e', providing the computer processor with a display screen to second-eye cornea distance; and the generating of the second display image is also based on the provided display screen to second-eye cornea distance. In some such embodiments, providing the computer processor with the display screen to first-eye and/or second-eye cornea distance comprises inputting a distance value or distance values as a parameter to the computer processor. Alternatively, in some such embodiments providing the computer processor with the display screen to first-eye cornea distance comprises determining a distance between the display screen and a cornea of the first eye of the subject, which determined distance is used to generate the display image and, in some embodiments, also the second display image. Similarly, when applicable, in some embodiments providing the computer processor with the display screen to second-eye cornea distance comprises determining a distance between the display screen and a cornea of the second eye of the subject, which determined distance is used to generate the second display image.

In a particularly preferred embodiments, there is provided a method useful for the treatment of existing refractive errors and/or prevention of the development of refractive errors in a human subject, comprising:

a. determining a gaze direction of a first eye of a subject viewing an image on a display screen and providing the determined gaze direction to a computer processor;

b. subsequent to 'a', based on the determined gaze direction of the first eye, with a computer processor generating a display image for display to the first eye on the display screen from a received digital base image, wherein:
 i. a central-vision portion of the display image that corresponds to a portion of the field of view of the first eye that includes the determined gaze direction is unmodified compared to a corresponding portion in the base image, and
 ii. a non-central vision portion of the display image that is different from the central-vision portion is modified so that visual characteristics of the non-central vision portion of the display image are changed compared to corresponding visual characteristics of a corresponding portion in the base image which modification degrades the image quality of the non-central vision portion relative to the corresponding portion in the base image, c. displaying the generated display image on the display screen so that the first eye and the second eye of the subject simultaneously view the display image on the display screen at a same location of the display screen, wherein a size of the central-vision portion of the display image corresponds to a field of view of the first eye of at least about 1° and not more than about 20° that includes the determined gaze direction of the first eye;

wherein the non-central vision portion completely surrounds the central-vision portion and is at least about 30% of the area of the display image that is not the central-vision portion;

wherein the modification which degrades the image quality of the non-central vision portion relative to the corresponding portion in the base image includes at least one modification selected from the group consisting of: reduced resolution; blurring and reduced contrast.

According to an aspect of some embodiments of the teachings herein, there is also provided a device for image processing and display, which in some embodiments is useful for the treatment of existing refractive errors and/or prevention of the development of refractive errors in a human subject, the device comprising:

a computer processor functionally associated with a display screen and an eye tracker, the eye tracker configured for determining a gaze direction of a first eye of a person viewing an image on the display screen and for providing a determined gaze direction to the computer processor;

the computer processor configured:

to generate a display image from a received digital base image based on a gaze direction of the first eye received from the eye tracker, wherein:
 i. a central-vision portion of the display image that corresponds to a portion of the field of view of the first eye that includes the determined gaze direction is either:
  unmodified compared to a corresponding portion in the base image; or
  modified so that visual characteristics of the central-vision portion of the display image are changed compared to corresponding visual characteristics of a corresponding portion in the base image which modification improves the image quality of the central-vision portion relative to the corresponding portion in the base image, and
 ii. a non-central vision portion of the display image that is different from the central-vision portion is either:
  unmodified compared to a corresponding portion in the base image; or
  modified so that visual characteristics of the non-central vision portion of the display image are changed compared to corresponding visual characteristics of a corresponding portion in the base image, wherein as a result of the generating, the image quality of the non-central vision portion of the display image is lower than the image quality of the central-vision portion of the display image; and to display the generated display image on the display screen so that the first eye of the person views the display image on the display screen.

In some embodiments, the display screen is configured so that the second eye of the subject can view a generated display image on a display screen (i.e., a different display screen or the same display screen). In some such embodiments, a generated display image is displayed at a same location of the display screen for both eyes to view simultaneously.

In some embodiments, the device further comprises:

an eye tracker configured for determining a gaze direction of a second eye of a person viewing the display screen and for providing a determined second eye gaze direction to the computer processor;

the computer processor further configured:

to generate a second display image from a received digital base image and based on a gaze direction of the second eye received from the eye tracker, wherein:
 i. a central-vision portion of the second display image that corresponds to a portion of the field of view of the second eye that includes the determined gaze direction is either:
  unmodified compared to a corresponding portion in the base image; or
  modified so that visual characteristics of the central-vision portion of the second display image are changed compared to corresponding visual characteristics of a corresponding portion in the base image which modification improves the image quality of the central-vision portion relative to the corresponding portion in the base image, and
 ii. a non-central vision portion of the second display image that is different from the central-vision portion is either:
  unmodified compared to a corresponding portion in the base image; or
  modified so that visual characteristics of the non-central vision portion of the second display image are changed compared to corresponding visual characteristics of a corresponding portion in the base image, wherein as a result of the generating, the image quality of the non-central vision portion of the second display image is lower than the image quality of the central-vision portion of the second display image; and to display the generated second display image on a display screen functionally associated with the computer processor so that the second eye of the person views the second display image on the display screen.

In such embodiments, the device is configured so that the second eye does not see a display image, and the first eye does not see the second display image. In some such embodiments, the second eye display screen and the display screen are two different physical components (e.g., some VR glasses). In some such embodiments, the second eye display screen and the display screen are the same physical screen, but the second display image and the display image are displayed on different locations of the screen (e.g., some VR glasses with a left eye/right eye partition), are displayed at the same place of the screen but at different times (e.g., shutter glasses) or are displayed at the same place at the same time on the same screen (e.g., using anaglyph or autostereoscopic methods).

In some embodiments, the same eye tracker is used to determine the gaze direction of both eyes. In some embodiments, the device comprises two different eye trackers, a first eye tracker to determine the gaze direction of the first eye and a second eye tracker to determine the gaze direction of the second eye.

In some embodiments, the central-vision portion of the display image corresponds to a field of view of the first eye that is centered around the determined gaze direction of the first eye. Similarly, when applicable, in some embodiments the central-vision portion of the second display image corresponds to a field of view of the second eye that is centered around the determined gaze direction of the second eye.

In some embodiments, the shape of the central-vision portion of the display image is a circle. Similarly, when applicable, in some embodiments, the shape of the central-vision portion of the second display image is a circle.

In some embodiments, the computer processor is configured so that a size of a central-vision portion of a display image corresponds to a field of view of the first eye of at least about 1° and not more than about 20° that includes a determined gaze direction of the first eye. In preferred embodiments, the computer processor is configured so that a size of a central-vision portion of a display image corresponds to a field of view of the first eye of not less than about 2° and not more than about 8° that includes a determined gaze direction of the first eye. Similarly, when applicable, in some embodiments, the computer processor is configured so that a size of a central-vision portion of a second display image corresponds to a field of view of the second eye of at least about 1° and not more than about 20° that includes a determined gaze direction of the second eye. In preferred embodiments, the computer processor is configured so that a size of a central-vision portion of a second display image corresponds to a field of view of the second eye of not less than about 2° and not more than about 8° that includes a determined gaze direction of the second eye.

In some embodiments, the computer processor is configured so that the central-vision portion of a generated display image is unmodified compared to a corresponding portion in a base image.

In some embodiments, the computer processor is configured to modify a base image so that visual characteristics of a central-vision portion of a generated display image are changed compared to corresponding visual characteristics of a corresponding portion in the base image which modification improves the image quality of the central-vision portion relative to the corresponding portion in the base image.

In some embodiments, the computer processor is configured so that a non-central vision portion of a generated display image and/or second display image is contiguous with the central vision portion. Additionally or alternatively, in some embodiments, the computer processor is configured so that a non-central vision portion of a generated display image and/or second display image at least partially surrounds a central vision portion. Additionally or alternatively, in some embodiments, the computer processor is configured so that a non-central vision portion of a generated display image or second display image completely surrounds the central-vision portion.

In some embodiments, the computer processor configured so that a radial dimensions of a non-central vision portion of a generated display image and/or second display image corresponds to a field of view of a respective eye of at least about 2°.

In some embodiments, the computer processor is configured so that a non-central vision portion of a generated display image is at least 1% of the area of the display image that is not the central-vision portion. In some embodiments, the computer processor is configured so that a non-central vision portion of a generated second display image is at least 1% of the area of the second display image that is not the central-vision portion.

In some embodiments, the computer processor is configured so that a non-central vision portion of a generated display image is at least about 30% of the area of the display image that is not the central-vision portion, and in some embodiments at least about 40%, at least about 50%, at least about 60%, at least about 70%, at least about 80%, at least about 90% at least about 95% and even about 100% of the area of the display image that is not the central-vision portion. Similarly, when applicable, in some embodiments the computer processor is configured so that a non-central vision portion of a generated second display image is at least about 30% of the area of the second display image that is not the central-vision portion, and in some embodiments at least about 40%, at least about 50%, at least about 60%, at least about 70%, at least about 80%, at least about 90% at least about 95% and even about 100% of the area of the second display image that is not the central-vision portion.

In some embodiments, the computer processor is configured so that a non-central vision portion of a generated display image and/or second display image is unmodified compared to a corresponding portion in the corresponding base image.

In some embodiments, the computer processor is configured to modify a base image so that visual characteristics of a non-central portion of a generated display image and/or second display image are changed compared to corresponding visual characteristics of a corresponding portion in the base image which modification change the image quality of the non-central vision portion relative to the corresponding portion in the base image.

Preferably, in some embodiments, the computer processor is further configured to modify a base image so that visual characteristics of a non-central portion of a generated display image and/or second display image are changed compared to corresponding visual characteristics of a corresponding portion in the base image which modification degrades the image quality of the non-central vision portion relative to the corresponding portion in the base image. In some such embodiments, the modification which degrades the image quality of a non-central vision portion of a display image and/or second display image relative to the corresponding portion in the base image includes at least one member selected from the group consisting of: reduced resolution; blurring; reduced contrast; reduced/increased brightness; reduced color intensity; reduced or changed color palette and combinations thereof. In preferred such embodiments, the modification which degrades the image quality of a non-central vision portion of a display image and/or second display image relative to the corresponding portion in the base image includes at least one member selected from the group consisting of: reduced resolution; blurring and reduced contrast.

In some embodiments, the configuration of the computer processor to generate a display image comprises configuration to generate a display image as an image data file and configuration to display a generated display image comprises configuration to display an image data file on the display screen. Similarly and when applicable, in some embodiments, the configuration of the computer processor to generate a second display image comprises configuration to generate a second display image as an image data file and configuration to display a generated secomd display image comprises configuration to display the image data file on the display screen.

In some embodiments, the configuration of the computer processor to generate and display a generated display image comprises:

configuration of the computer processor to generate a mask image comprising a non-degrading central vision portion and a degrading non-central vision portion; and configuration to display a generated mask image together with a base image on the display screen so as to generate and display a display image.

Similarly and when applicable, in some embodiments, the configuration of the computer processor to generate and display a generated second display image comprises:

configuration of the computer processor to generate a second mask image comprising a non-degrading central vision portion and a degrading non-central vision portion; and configuration to display a generated second mask image together with a base image on the display screen so as to generate and display a second display image.

In some embodiments, the computer processor is further configured to generate a display image and/or a second display image also based on a provided display screen to first-eye cornea distance. Similarly, when applicable, in some embodiments, the computer processor is further configured to generate a second display image also based on a provided display screen to second-eye cornea distance.

In some embodiments, the display screen to first-eye cornea distance and/or the display screen to second-eye cornea distance is provided as a parameter.

In some embodiments the device further comprises a component for determining a display screen to first-eye cornea distance and for providing a determined distance to the computer processor; and wherein the computer processor is further configured to generate a display image and/or a second display image also based on a provided display screen to first-eye cornea distance. Similarly, when applicable, the device comprises a component for determining a display screen to second-eye cornea distance and for providing a determined distance to the computer processor; and wherein the computer processor is further configured to generate a second display image also based on a provided display screen to second-eye cornea distance. In some embodiments, the same component is used to determine the display screen to cornea distance for both eyes. In some embodiments, the device comprises two different components, a first component to determine a display screen to first-eye cornea distance and a second component to determine the display screen to second-eye cornea distance.

In a particularly preferred embodiment, there is provided a device for image processing and display, comprising:

a computer processor functionally associated with a display screen and an eye tracker, the eye tracker configured for determining a gaze direction of a first eye of a person viewing the display screen and for providing a determined gaze direction to the computer processor;

the computer processor configured:

to generate a display image from a received digital base image based on a gaze direction of the first eye received from the eye tracker, wherein:

i. a central-vision portion of the display image that corresponds to a portion of the field of view of the first eye that includes the determined gaze direction is unmodified compared to a corresponding portion in the base image; and ii. a non-central vision portion of the display image that is different from the central-vision portion is modified so that visual characteristics of the non-central vision portion of the display image are changed compared to corresponding visual characteristics of a corresponding portion in the base image which modification degrades the image quality of the non-central vision portion relative to the corresponding portion in the base image, to display a generated display image on the display screen so that the first eye of the person views the display image on the display screen;

wherein the computer processor is configured so that the size of the central-vision portion of a display image corresponds to a field of view of the first eye of at least about 1° and not more than about 20° that includes the determined gaze direction of the first eye;

wherein the computer processor is configured so that a non-central vision portion of a generated image completely surrounds the central-vision portion of the generated image and is at least about 30% of the area of the display image that is not the central-vision portion;

wherein the computer processor is configured so that the modification which degrades the image quality of the non-central vision portion of a generated display image relative to the corresponding portion in the base image includes at least one modification selected from the group consisting of: reduced resolution; blurring and reduced contrast.

Herein, a display image and, if present, a second-display image include a central-vision portion and a non-central vision portion. In some instances in the priority document, the non-central vision portion is also called the first portion and the central-vision portion is also called the second portion.

BRIEF DESCRIPTION OF THE SEVERAL VIEWS OF THE DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1:
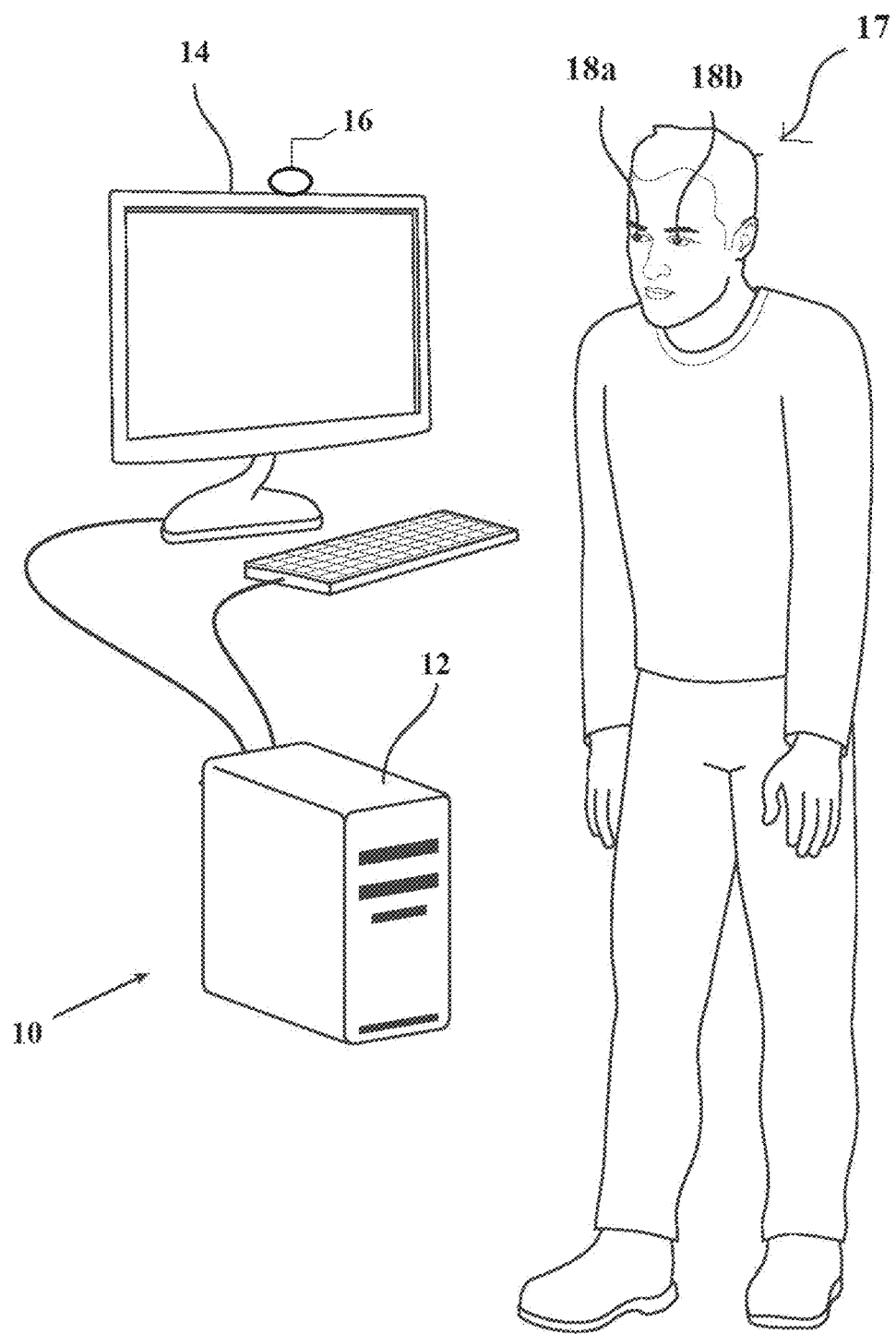
FIG. 1 is a schematic depiction of a device according to the teachings herein.

Some embodiments, relates to the field of image processing and display, and, more particularly but not exclusively, to methods and devices useful for image processing and display of such images to a human subject. Some embodiments of the invention herein relate to methods and devices useful the field of ophthalmology and, in some particular embodiments, useful for the non-invasive treatment and/or prevention of refractive errors in humans, particularly, myopia, hyperopia and astigmatism.

As discussed above, subsequent to birth, the human eye grows from about 1.8 cm long to about 2.5 cm long. In ideal situations, the growth of the eye is such that light entering the eye through the pupil is focused on the foveal plane, thereby achieving emmetropia. In less ideal situations, the growth of the eye is such that light entering the eye through the pupil is not focused on the foveal plane, leading to a refractive error such as myopia, hyperopia and astigmatism.

It would be useful to have methods and devices that at least partially prevent and/or treat extant refractive errors during the period when the human eye grows so that in adulthood a treated human has a reduced magnitude of refractive error or has no refractive error at all. Preferably, such methods and devices are non-invasive.

Studies have shown that the growth of human and monkey eyes is influenced by the light falling on the retina, see for example Read et al "Light exposure and eye growth in childhood" in Invest Ophthalmol Vis Sci 2015, 56(11), 6779-6787.

Other studies performed on monkeys have shown that the influence of light on eye-growth remains even when there is no connection between the optic nerve and the brain: apparently the light falling on the retina leads to local chemical and biological changes that effect the eye growth.

Herein is also disclosed a method of image processing to generate a display image which is displayed to a person.

Herein is disclosed a non-invasive method useful for the non-invasive treatment of existing refractive errors and/or prevention of the development of refractive errors in a human subject, particularly myopia, hyperopia and astigmatism. Also disclosed is a device useful for implementing the method.

In some embodiments, the method comprises generating and displaying a display image on a screen to be viewed by an eye of a human where a central vision portion of the display image and/or a different non-central vision portion of the display image has/have been modified so that the image quality of the non-central vision portion of the second display image is lower than the image quality of the central-vision portion of the second display image.

The methods can be implemented using any device or combination of devices. For example, a single computer processor to implement all actions that require a computer processor, or at least two computer processors each one performing at least some of the actions that require a computer processor. In some preferred embodiments, the methods are implemented using an embodiment of a device according to the teachings herein, for example, as described in the "Summary of the Invention" section, hereinabove.

In FIG. 1 is depicted a device 10 for implementing some embodiments of the teachings herein, device 10 comprising a computer processor inside a box 12 functionally associated with a display screen 14 and an eye tracker 16. A human subject 17 having a first eye 18a and a second eye 18b views an image displayed on display screen 14.

A flowchart 20 of an embodiment of a method according to the teachings herein is depicted in FIG. 2.

According to an aspect of some embodiments of the teachings herein, there is provided a method, comprising:

a. in box 22, determining a gaze direction of a first eye 18a of a subject 17 viewing an image on a display screen 14 (using eye tracker 16) and providing the determined gaze direction to a computer processor;

b. subsequent to 'a', in box 26 based on the determined gaze direction of the first eye 18a, with a computer processor generating a display image for display to the first eye 18a on the display screen 14 from a received digital base image (received in box 24), wherein:

i. a central-vision portion of the display image that corresponds to a portion of the field of view of the first eye 18a that includes the determined gaze direction is either:

unmodified compared to a corresponding portion in the base image; or modified so that visual characteristics of the central-vision portion of the display image are changed compared to corresponding visual characteristics of a corresponding portion in the base image which modification improves the image quality of the central-vision portion relative to the corresponding portion in the base image, and ii. a non-central vision portion of the display image that is different from the central-vision portion is either:

unmodified compared to a corresponding portion in the base image; or modified so that visual characteristics of the non-central vision portion of the display image are changed compared to corresponding visual characteristics of a corresponding portion in the base image, wherein as a result of the generating, an image quality of the non-central vision portion of the display image is lower than the image quality of the central-vision portion of the display image; and c. in box 28, displaying the generated display image on the display screen 14 so that the first eye 18*a* of the subject 17 views the display image on the display screen 14.

Technical Aspects of Generation of Display Image

As noted above, a display image is generated from a base image based on a determined gaze direction of a subject's eye and the generated display image is displayed on a display screen.

As schematically depicted in a flowchart 30 in FIG. 2B, in some embodiments, the generating of a display image and the displaying of the generated display image are two separate steps where the display image is first generated and subsequently displayed. Accordingly, in some embodiments generating the display image comprises generating the display image as an image data structure (box 26*a* in FIG. 2B) and displaying the generated display image is subsequently displaying the image data structure on a display screen (box 26*b* in FIG. 2B). Typically, after being generated the image data structure is temporarily stored in a computer memory (e.g., RAM, ROM or a combination thereof) and subsequently sent to a GPU (graphics processing unit) for display on the display screen.

As schematically depicted in a flowchart 32 in FIG. 2C, in some alternative embodiments, generating a display image and displaying the generated image is comprises first generating a partially-transparent mask image and subsequently displaying the base image and the mask image at the same time on the display screen. The display of the base image and the mask image at the same time on the display screen is concurrent generation and display of the display image on the display screen. Accordingly, in some embodiments: generating the display image comprises generating a mask image comprising a non-degrading central vision portion and a degrading non-central vision portion (box 26' in FIG. 2C); and subsequently displaying the mask image together with the base image on the display screen so as to generate and display the display image (box 26" in FIG. 2C. Some such embodiments are implemented on a computer operating with windows as a GUI (graphic user interface). After generation of the mask image (box 26') the mask image and the base image are both sent to the GPU and are simultaneously displayed on the display screen in the usual way (box 26"). The net effect is that a person viewing the display screen sees a display image in accordance with the teachings herein, where the display image is the combination of the base image and the mask image. In typical such embodiments, the portion of the mask image that corresponds to the central-vision portion is a non-degrading central vision portion (e.g., is "transparent"): when the base image and the mask image are displayed together, the non-degrading central vision portion of the mask image does not effect the appearance of the central vision portion of the base image so that the portions of the base image corresponding to the central-vision portion appears to a subject to be unmodified. In contrast, the portion of the mask image that corresponds to the non-central vision portion is a degrading non-central vision portion: when the base image and the mask image are displayed together, the degrading non-central vision portion of the mask image changes the appearance of the central vision portion of the base image, thereby degrading the appearance of central vision portion. In contrast, the portion of the mask image that corresponds to the non-central vision portion is degrading (e.g., partially transparent) so when the mask image and the base image are displayed together, the portions of the base image corresponding to the central-vision portion is seen "overlaid" with the mask image and appears to be modified so as to degrade the image quality thereof.

Effect of Viewing the Display Image

The methods can be implemented on a subject of any age. For human subjects, the preferred age is typically between 2 and 18 years during which time the physical structure of the eye can more easily change as a result of visual stimuli.

Without wishing to be held to any one theory, it is currently believed that implementing the methods effects biological changes that change the growth of the components of the eye, for example, physical growth of the eye and the development of the optical portions of the eye, which in some embodiments non-invasively treat and/or prevent the development of refractive errors such as myopia, hyperopia and astigmatism.

Without wishing to be held to any one theory, it is currently believed that the more a subject views display images on a display screen in accordance with the teachings herein, the greater the positive effects will be felt. Since it is believed that one of the major causes of refractive errors such as myopia in children is indoor viewing of images on a screen, in preferred embodiments the method is implemented on as many as possible, preferably all, display screens that a subject to be treated views during a day.

Specifically, it is currently believed that when an eye views a generated display image, the non-central portion of the retina of the first eye perceives the non-central vision portion of the display image and such perception has an effect on the growth and physical development of the eye, for example, the length of the eyeball and the curvature of the cornea. As a result, for a subject susceptible to the development of refractive errors such as myopia, hyperopia and astigmatism, application of some embodiments of the method according to the teachings herein prevents the development of a refractive error or reduces the ultimate severity of a developed refractive error. Similarly, for a subject already suffering from a refractive error such as myopia, hyperopia or astigmatism, application of some embodiments if the method according to the teachings herein stops the progression of an extant refractive error or even reduces the severity of an extrant refractive error.

Application of the Method to a Single Eye of the Subject

In some embodiments, the method is applied to only one eye of a subject, that is to say, only one eye (the first eye) views a display image generated from a received digital base image. In such embodiments, only the first eye undergoes the positive effects of perceiving the two portions of a display image according to the teachings herein. In such embodiments, the display image is displayed on a screen so that the first eye views the display image but the second eye cannot view the display image. Such an embodiment can be depicted in a modification of FIG. 1 where second eye 18*b* is covered with an eye patch so that only first eye 18*a* can view images displayed on display screen 14. Such a modification is not depicted for the sake of brevity.

Display of the Same Display Image to Both Eyes

In some preferred embodiments, the method is applied concurrently to both eyes of a subject so that both the first eye and the second eye view the same display image. In such embodiments, both the first eye and the second eye undergo the positive effects of perceiving the two portions of a display image according to the teachings herein. Accordingly, in some embodiments the method further comprises: displaying the generated display image on a display screen so that the second eye of the subject views the display image (i.e., the same display screen as the first eye or a display screen that is different from the display screen for the first eye, for example, on a VR headset having two separate screens, one for each eye).

In some such embodiments, the display image is displayed at the same location of the same display screen for both eyes to view simultaneously. Such embodiments are suitable, for example, when the method is implemented on a computer or television display screen that both eyes view simultaneously. Such an embodiment is depicted in FIG. 1, where first eye 18*a* and second eye 18*b* can simultaneously see the same display image displayed on display screen 14.

Alternatively, in some embodiments the display image is alternatingly (and not simultaneously) displayed on the same screen at the same place for each eye to view for example, on a display screen configured for alternating display when the subject is wearing shutter glasses. Such an embodiment is depicted in FIG. 2, where subject 17 is wearing glasses 34 which are shutter glasses which operation is coordinated with an alternating display of a display image on display screen 14 as known in the art, so that each one of eyes 18*a* and 18*b* alternatingly see the same display image displayed on display screen 14.

Alternatively, in some embodiments, the display image is displayed on the same screen, but at a different place for each eye to view, for example, when the method is implemented on a VR headset including a single screen which is partitioned into a left-eye portion and a right-eye portion. Such an embodiment is not depicted in the figures for the sake of brevity.

Alternatively, in some embodiments, the display image is displayed on a different screen for each eye to view, for example, when the method is implemented on a VR headset where each eye is provide with an own, physically distinct, display screen. Such an embodiment is not depicted in the figures for the sake of brevity.

Display of a Different Image to Each Eye

In some embodiments, the method is applied so that the first eye views the display image as described above and the second eye views a second display image that is different from the display image. Such embodiments allow both the first eye and the second eye to undergo the positive effects of perceiving the two portions of a display image according to the teachings herein. Accordingly, in some embodiments, the method further comprises, concurrently with 'a' and 'b' as recited above for the first eye:

d. determining a gaze direction of a second eye of the subject (person) viewing a second eye display screen and providing the determined gaze direction to a computer processor;

e. subsequent to 'c', based on the determined gaze direction of the second eye, with a computer processor generating a second display image for display to the second eye on the second eye display screen from the received digital base image, wherein:

i. a central-vision portion of the second display image that corresponds to a portion of the field of view of the second eye that includes the determined gaze direction is either:
unmodified compared to a corresponding portion in the base image; or
modified so that visual characteristics of the central-vision portion of the second display image are changed compared to corresponding visual characteristics of a corresponding portion in the base image which modification improves the image quality of the central-vision portion relative to the corresponding portion in the base image, and ii. a non-central vision portion of the second display image that is different from the central-vision portion is either:
unmodified compared to a corresponding portion in the base image; or
modified so that visual characteristics of the non-central vision portion of the second display image are changed compared to corresponding visual characteristics of a corresponding portion in the base image, wherein as a result of the generating, the image quality of the non-central vision portion of the second display image is lower than the image quality of the central-vision portion of the second display image; and f. displaying the generated second display image on the second eye display screen so that the second eye of the subject (person) views the second display image on the second eye display screen.

In such embodiments, the display image is displayed on a screen so that the second cannot see the display image and the second display image is displayed on a screen so that the first eye cannot see the second display image.

Figure 2A:
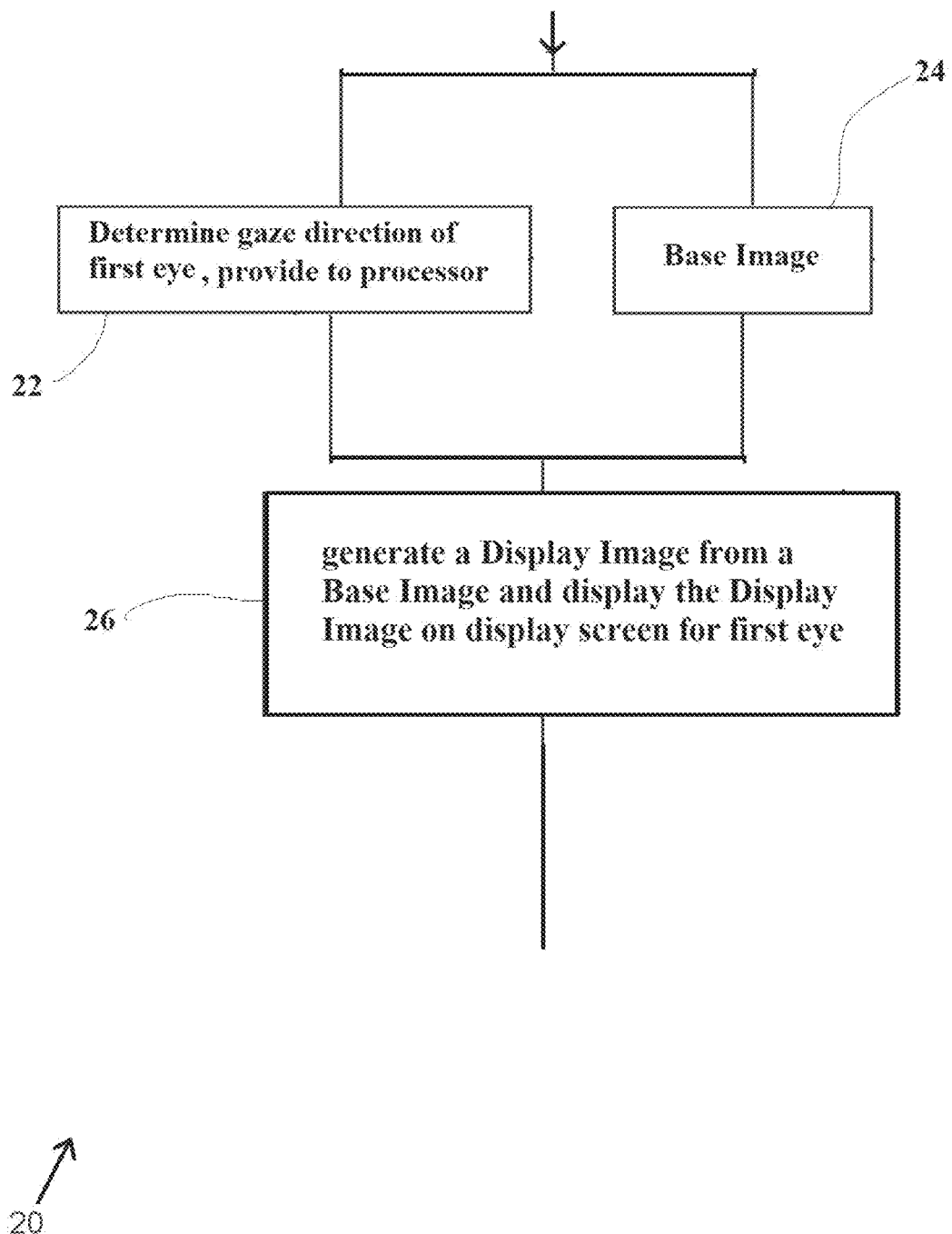
FIGS. 2A, 2B and 2C depict flow charts that schematically depict some embodiments of methods according to the teachings herein.
Figure 2B:
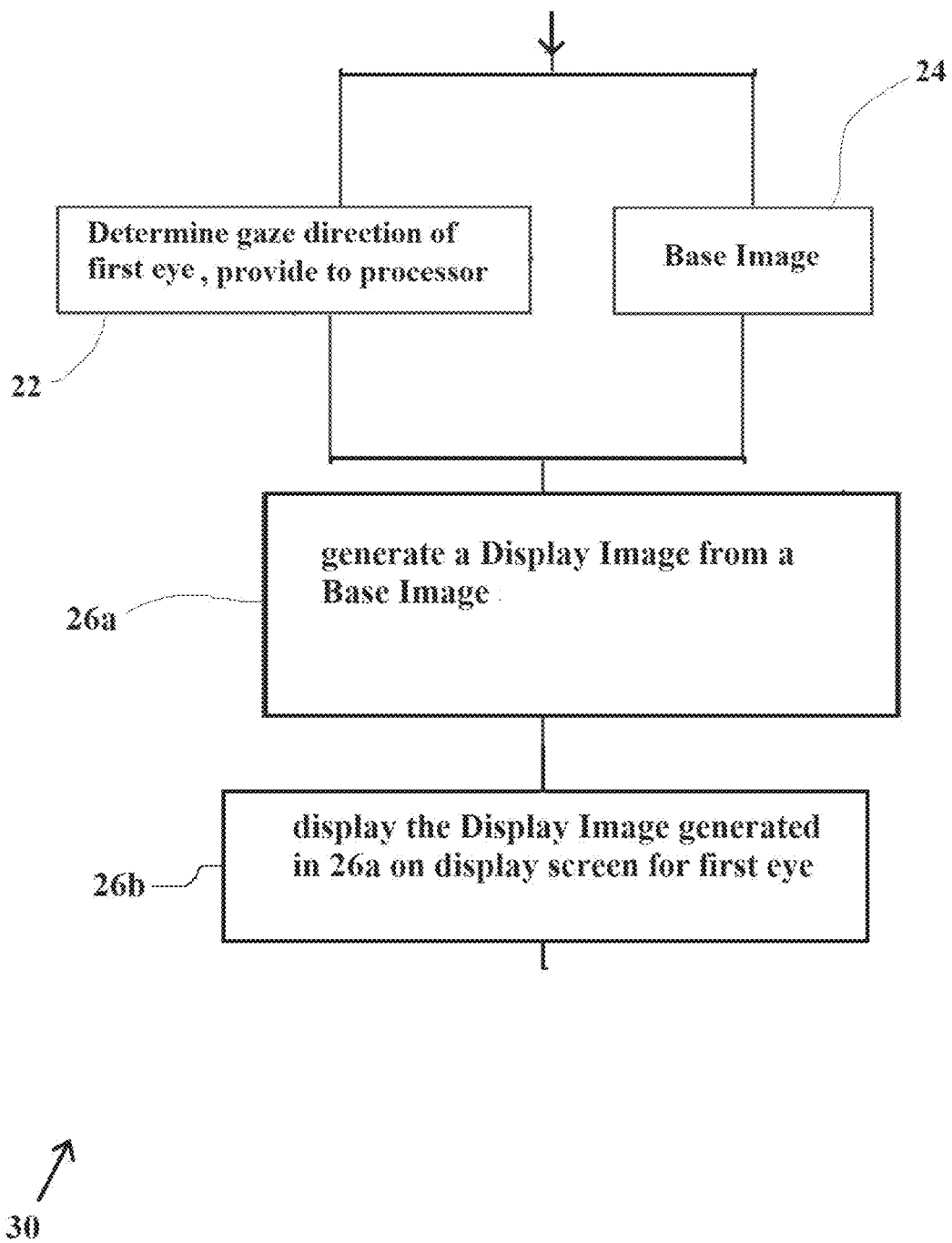
Figure 2C:
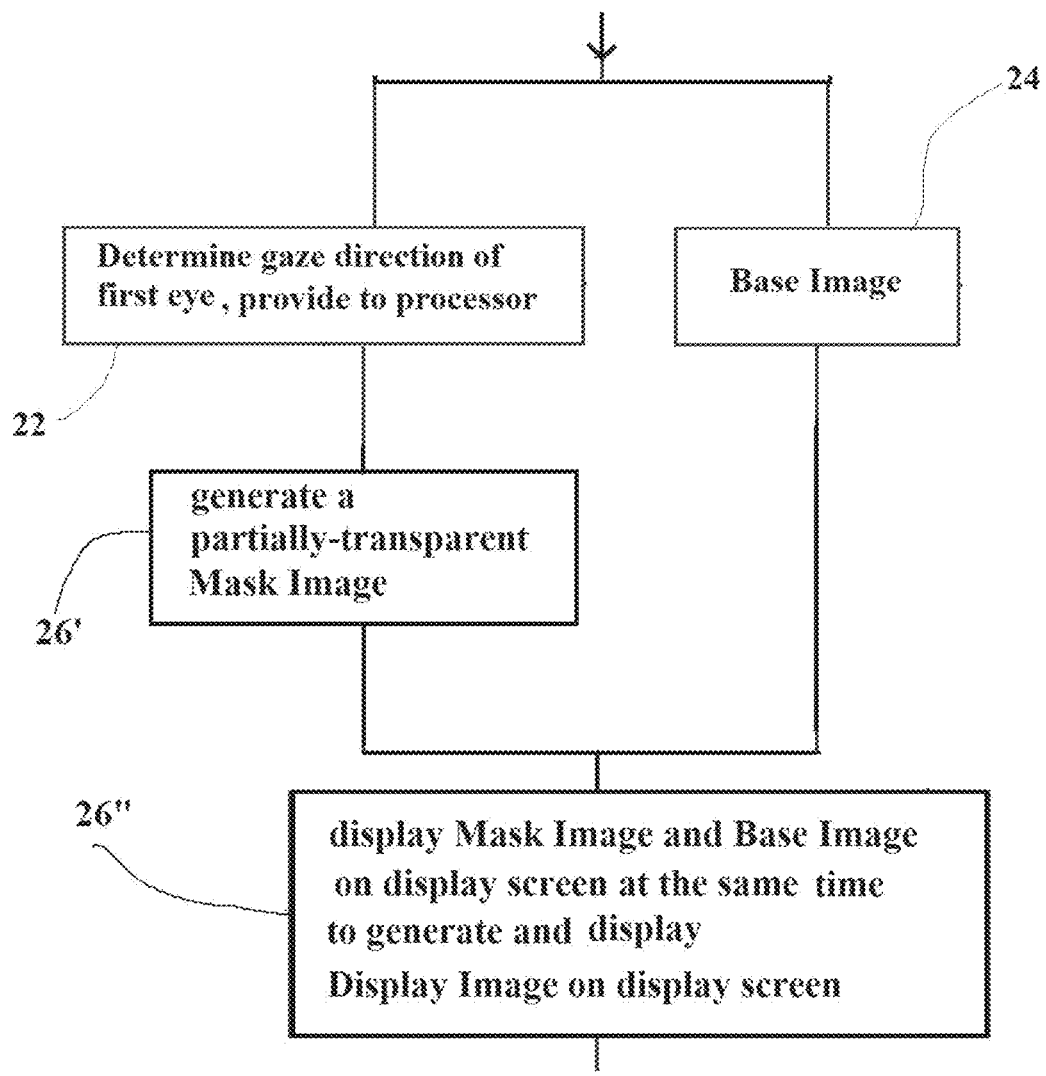

For the sake of brevity, a separate flow chart relating to the process for generating a second display image is not presented herein as the process is substantially the same as for generating a display image as depicted in flowchart 20 in FIG. 2A, flowchart 30 in FIG. 2B and flowchart 32 in FIG. 2C.

Figure 3:
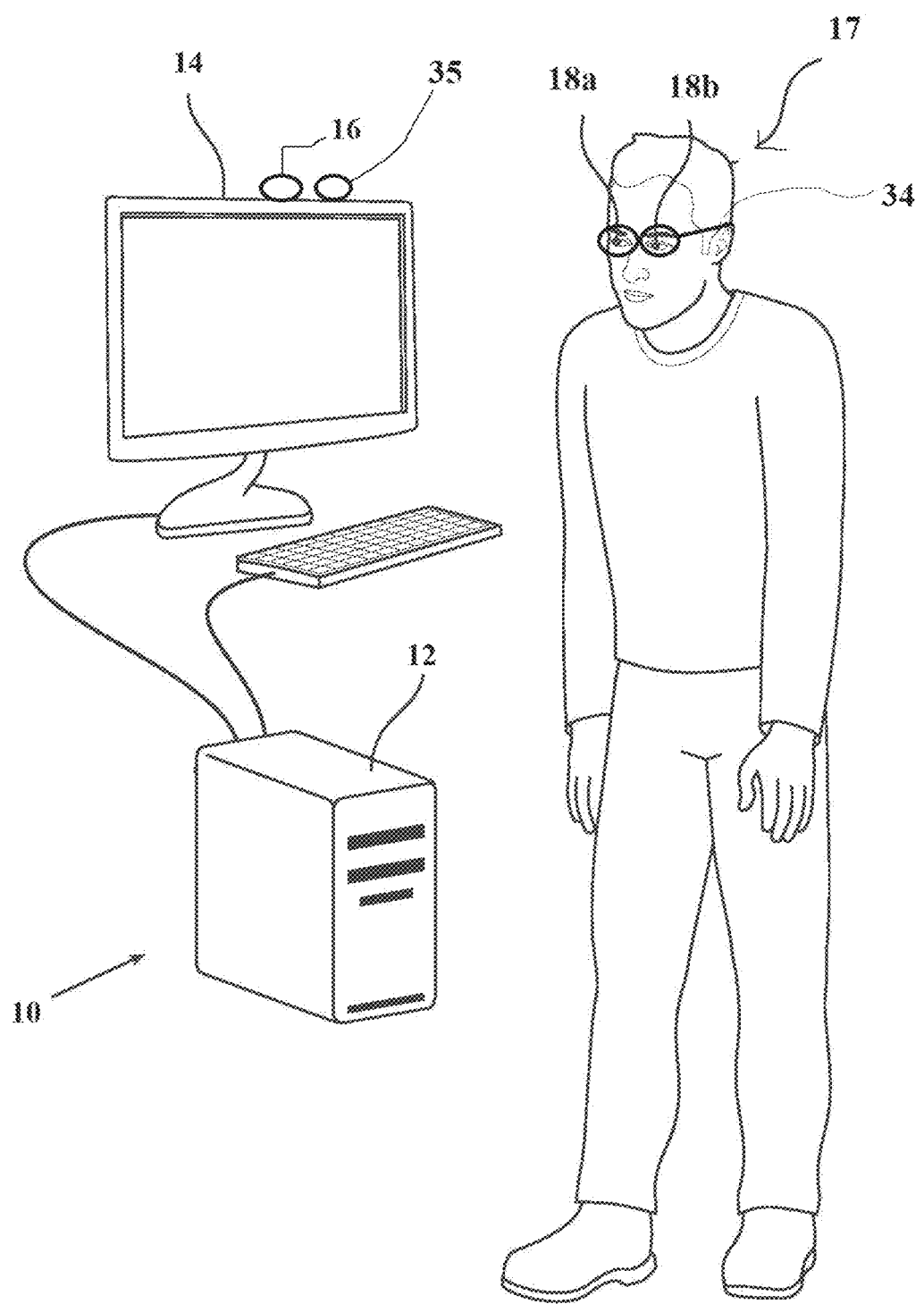
FIG. 3 is a schematic depiction of a device according to the teachings herein.

In some embodiments, the base image is a stereoscopic base image comprising two subimages that constitute a stereoscopic image pair, a left-eye base subimage and a right-eye base subimage. In such embodiments, the display image and the second display image are each generated from the appropriate base subimage. For example, when the first eye is the left eye, the display image is generated from the left-eye base subimage and the second display image is generated from the right-eye base subimage. Alternatively, when the first eye is the right eye, the display image is generated from the right-eye base subimage and the second display image is generated from the left-eye base subimage. In such embodiments, the display image and the second display image are stereoscopically displayed to a subject in an suitable way, for example, on a display screen configured for autostereoscopy (which embodiment is represented by FIG. 1), on a display screen configured for alternating display to a subject wearing shutter glasses (which embodiment is represented by FIG. 3 when glasses 34 are shutter glasses), on a VR headset where each eye is provided with an own screen or an own part of a screen (not depicted for the sake of brevity), or when the display image and the second display image are an anaglyph pair configured to be displayed to a user wearing anaglyph glasses (which embodiment is represented by FIG. 3 when glasses 34 are anaglyph glasses). In FIG. 3 is also depicted a range-finder 35 (e.g., XL-Maxsonar-EZ2 by Maxbotix, Inc, Fort Mill, S.C., USA which is useful for implementing some embodiments of the teachings herein.

Alternatively, in some embodiments, the base image is a monoscopic base image. In some such embodiments the display image and the second display image are displayed on the same screen for a respective eye to view for example, on a display screen configured for alternating display when the subject is wearing shutter glasses (which embodiment is represented by FIG. 3 when glasses 34 are shutter glasses), when the display image and the second display image are an anaglyph pair configured to be displayed to a user wearing anaglyph glasses (which embodiment is represented by FIG.

3 when glasses 34 are anaglyph glasses), when the display screen is configured for autostereoscopy (which embodiment is represented by FIG. 1), or when the method is implemented on VR headset including a single screen which is partitioned into a left-eye portion and a right-eye portion (not depicted for the sake of brevity).

Alternatively, in some embodiments, the display image and the second display image are displayed on a different screen for each eye to view, for example, when the method is implemented on a VR headset where each eye is provide with an own, physically distinct, display screen (not depicted for the sake of brevity).

In some such embodiments, the non-central portions of the display image and of the second display image are the same size. Alternatively, in some embodiments, the non-central portions of the display image and of the second display image are of different sizes.

In some such embodiments, the non-central portions of the display image and of the second display image are the same shape. Alternatively, in some embodiments, the non-central portions of the display image and of the second display image are of different shapes.

In some such embodiments, the central-vision portions of the display image and of the second display image are the same size. Alternatively, in some embodiments, the central-vision portions of the display image and of the second display image are of different sizes.

In some such embodiments, the central-vision portions of the display image and of the second display image are the same shape. Alternatively, in some embodiments, the central-vision portions of the display image and of the second display image are of different shapes.

In some such embodiments, the modifications performed on the base image to yield the display image are different from the modifications performed on the base image to yield the second display image. Some such embodiments are used when it is desired to have a different effect on the development of the respective eye.

Alternatively, in some such embodiments, the modifications performed on the base image to yield the display image are the same modifications performed on the base image to yield the second display image. It is important to note that in such embodiments, the display image and the second display image are not necessarily identical. For example, the location of the modifications is based on the determined gaze directions of the two eyes which are not necessarily the same. For example, in embodiments where the base image is a stereoscopic base image the two display images are necessarily different.

Display Screen

A generated display image is displayed on a display screen so that the first eye (and in some embodiments, also the second eye) of a subject views the generated display image and, in some embodiments, a generated second display image is displayed on a display screen so that the second eye of the subject views the generated second display image.

In some embodiments, the method is implemented on a display screen (e.g., LCD, LED, plasma) intended to be viewed from at least 10 cm distant (as measured from a subject's cornea to the screen surface). In some such embodiments, the display screen has a surface area of at least 100 cm$^2$. Typical such embodiments are implemented using the display screen of a computer, television, smartphone or tablet. In typical such embodiments a single display screen is used to display images to both the first eye and the second eye. Such embodiments are depicted in FIGS. 1 and 3.

In some embodiments, the displaying includes generating a display image and a second display images as an anaglyph pair and displaying the two generated images on a display screen (simultaneous or alternatingly) as an anaglyph pair to a subject wearing anaglyph glasses.

In some embodiments, the displaying includes alternatingly displaying a generated image to each eye of a subject wearing shutter glasses, where the rate and duration of the alternating display is coordinated with the activation of the shutter glasses so that each eye sees an appropriate generated image. As noted above, in some embodiments both eyes see the same generated display image while in alternative embodiments a first eye see a display image and a second eye sees a second display image.

In some embodiments, the displaying is implemented on a display screen configured for autostereoscopy (also known as, glasses-free 3D) and a display image is generated and displayed according to an autostereoscopic method as is known to a person having ordinary skill in the art. Similarly, in some embodiments the displaying is implemented on a display screen configured for autostereoscopy and a display image and a second display image are generated and displayed according to an autostereoscopic method as is known to a person having ordinary skill in the art.

In some embodiments, the method is implemented using the display screen or screens of a VR (virtual reality) headset. Typically, a VR headset is a device where at least 80% of the field of view of a subject receives visual information from a screen or screens of the headset. A screen or screens of a VR headset are of any technology (e.g., LED, LCD, plasma). Typically, but not necessarily, the screen or screens of a VR headset are positioned not more than 15 cm distant from a subject's cornea.

In some embodiments, a VR headset has a display screen for display of images to the left eye and a different display screen for display of images to the right eye. In such embodiments, a display image and a corresponding second display image are each displayed on a different display screen of the VR headset, each image on an appropriate display screen, thereby ensuring that the second display image is displayed on a screen so that the first eye does not see the second display image and the display image is displayed on a screen so that the second eye does not see the display image.

In some embodiments, a VR headset has a single display screen for display of images to both eyes, where the left part of the display screen is used for displaying images only to the left eye and the right part of the display screen is used for displaying images only to the right eye. In such embodiments, the display image and the second display image are each displayed on a different part of the screen of the VR headset, each image on an appropriate part of the display screen, thereby ensuring that the second display image is displayed on the display screen so that the first eye does not see the second display image and the display image is displayed on the display screen so that the second eye does not see the display image.

Rate of Displaying an Image

Typically, determining the gaze direction of an eye, generating a display image (and, if relevant, a second display image) from a received digital base image and displaying the generated display image (and, if applicable, the generated second display image) is performed repeatedly, in preferred embodiments at a rate of not less than 10 Hz and more preferably not less than 30 Hz.

Determining the gaze direction of one or two eyes of a human subject is well-known and is performed using any suitable device or a combination of devices, for example, commercially-available eye trackers such as from Tobii (Danderyd Municipality, Sweden).

In some embodiments, multiple display images are generated based on a single determined first-eye gaze direction and, if applicable, multiple second display images are generated based on a single determined second-eye gaze direction.

In some instances, the received base image is a still image (e.g., text) that is intended to be displayed on a display screen for a relatively long time, e.g., longer than $\frac{1}{30}^{th}$ of a second, e.g., for at least 0.5 seconds, for at least 1 second. In such instances, a series of different display images are generated from the same base image and displayed on the display screen, each different display image generated based on a different determined gaze direction, and, if applicable, a series of different second display images are generated from the same base image and displayed on the display screen.

In some instances, the received base image is a frame of a video having a given frame rate (fps—number of frames per second). In preferred such instances, a single display image (and, if applicable, a single second display image) is generated and displayed on the display screen from a single corresponding frame.

In some preferred such embodiments, the rate of determining the gaze direction of the first eye (and, if applicable, of the second eye), generating a display image from the base image (and, if applicable, generating a second display image from the base image), and displaying the generated display image (and, if applicable, displaying the generated second display image) is performed at the frame rate of the video.

Alternatively, in some embodiments, the rate of determining the gaze direction of the first eye (and, if applicable, of the second eye), generating a display image from the base image (and, if applicable, generating a second display image from the base image), and displaying the generated display image (and, if applicable, displaying the generated second display image) is performed at a rate that is less than the frame rate of the video.

Alternatively, in some embodiments, the rate of determining the gaze direction of the first eye (and, if applicable, of the second eye), generating a display image from the base image (and, if applicable, generating a second display image from the base image), and displaying the generated display image (and, if applicable, displaying the generated second display image) is performed at a rate that is faster than the frame rate of the video. In some such embodiments, some frames of the video are used as a base image for generation of more than one display image (and, if applicable, more than one second display image).

Received Digital Base Image

The base image is any suitable image for display to the subject. As noted above, in some embodiments the base image is a monoscopic image and in some embodiments the base image is a stereoscopic image pair comprising a left eye base subimage and a right eye base subimage. In some embodiments, the base image is a still image and in some embodiments the base image is a frame from a video. In some embodiments, the base image is all or a portion of a scene that the subject is viewing from which the base image is isolated. In some embodiments, the base image is all or a portion of a stored scene, e.g., a scene that is a frame or part of a frame from a movie or video game. In some embodiments, the base image is all or a portion of an acquired scene (e.g., a scene that is acquired by one or more cameras, in some embodiments in real time) from which a display image is generated and displayed to the subject, in preferred embodiments, in real time.

Generating a Display Image from a Received Digital Base Image

Figure 4A:
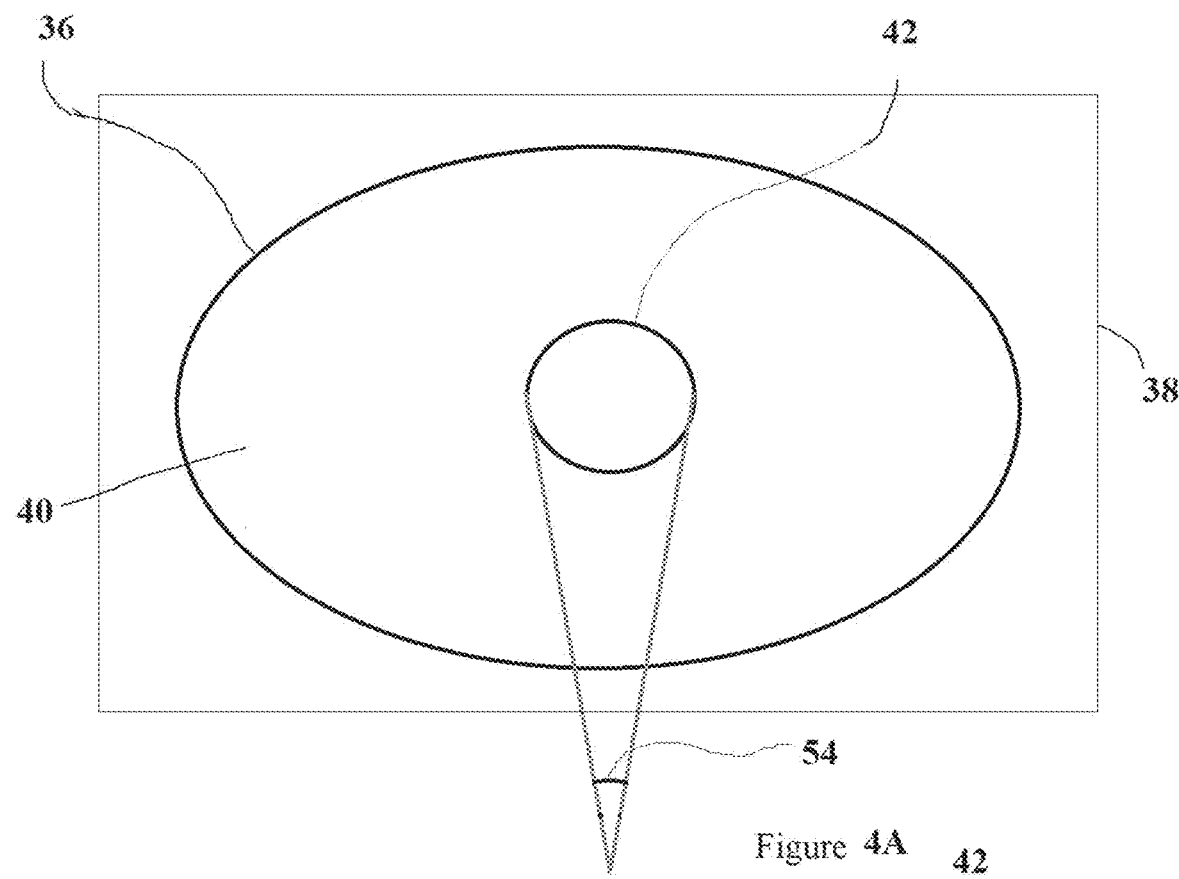
FIG. 4A is a schematic depiction of a field of view of an eye according to an embodiment of the teachings herein.
Figure 4B:
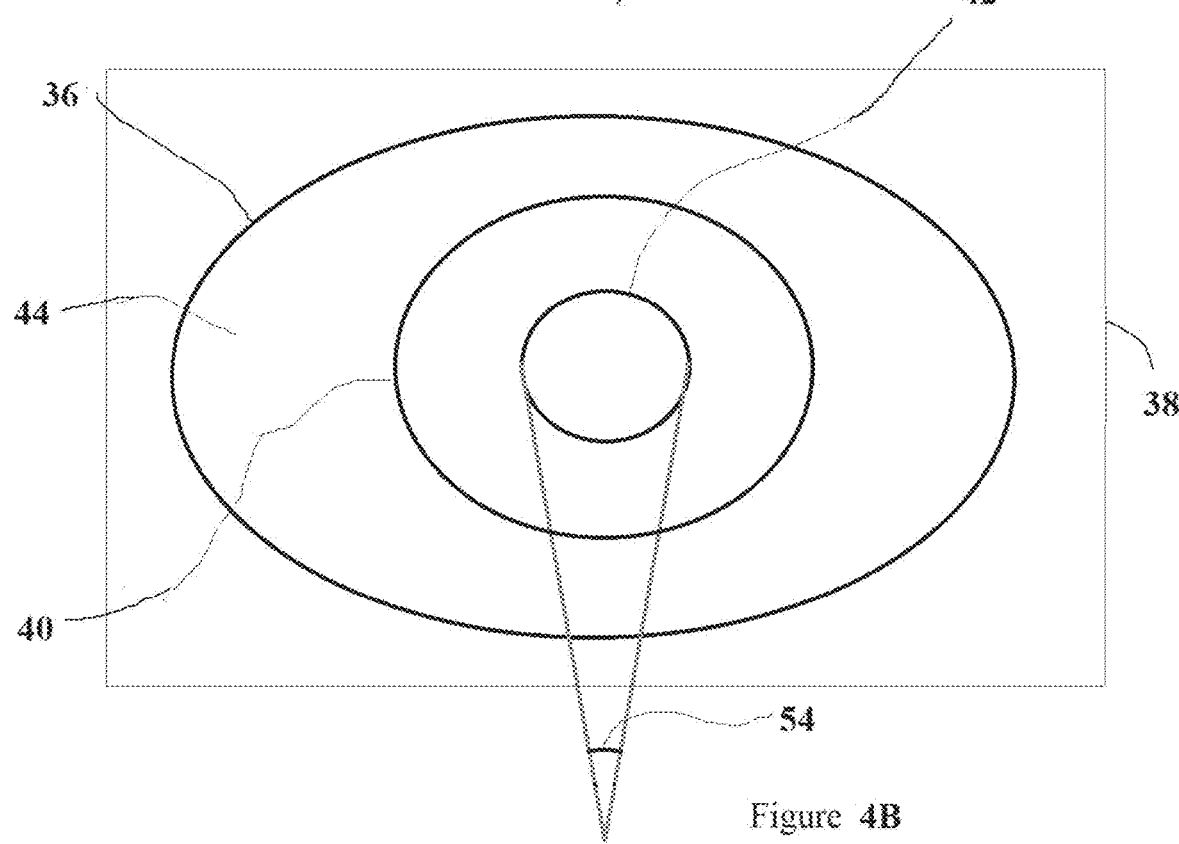
FIG. 4B is a schematic depiction of a field of view of an eye according to an embodiment of the teachings herein.

As depicted in FIGS. 4A and 4B, according to the method of the teachings herein a field of view 36 of an eye (either a first eye or a second eye) viewing a scene 38 is divided into at least two portions: a first non-central portion 40 and a second central portion 42. In FIG. 4B, an additional third non-central portion 44 of field of view 36 is also indicated.

A display image or a second display image according to the teachings herein comprises a non-central vision portion that corresponds to a non-central portion of the field of view of a respective eye, that is to say, is displayed on a display screen so that a non-central portion of the field of view (44 in FIGS. 4A and 4B) of a viewing eye perceives the non-central vision portion of the display image or of the second display image.

A display image or a second display image also comprises a central-vision portion that corresponds to a central portion of the field of view of an eye, that is to say, is displayed on a display screen so that a central portion of the field of view (42 in FIGS. 4A and 4B) of a viewing eye perceives the central-vision portion of the display image or of the second display image.

Figure 5A:
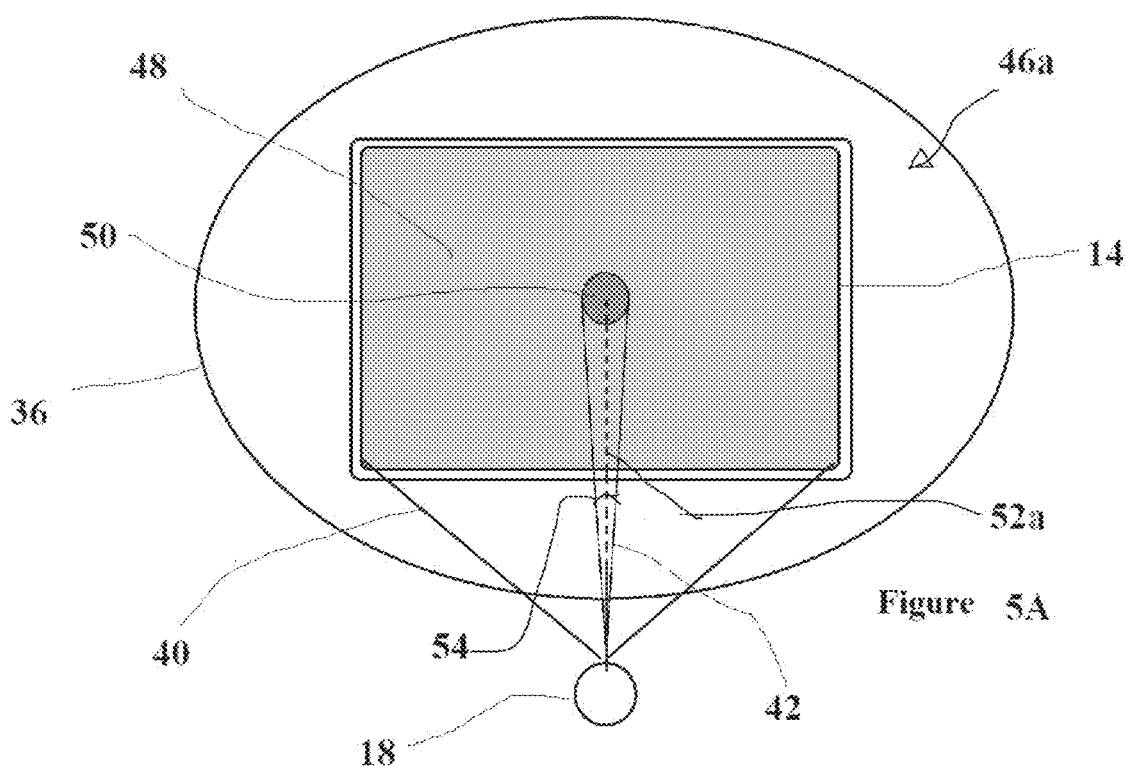
FIG. 5A is a schematic depiction of a display image or a second display image according to an embodiment of the teachings herein.

In FIG. 5A is depicted an eye 18 (a first eye or a second eye) viewing an image 46a (a display image or a second display image) displayed on a display screen 14 (e.g., a computer display screen). A field of view 36 of eye 18 is larger than display screen 14. Image 46a displayed on display screen 14 comprises two portions, a non-central vision portion 48 of image 46a which corresponds to a non-central vision portion 40 of field of view 36 of eye 18 and a central-vision portion 50 of image 46a which corresponds to a central vision portion 42 of field of view 36 of eye 18. For generation of image 46a from a base image, a gaze direction 52a was determined for eye 18 immediately prior to generation of image 46a.

Figure 5B:
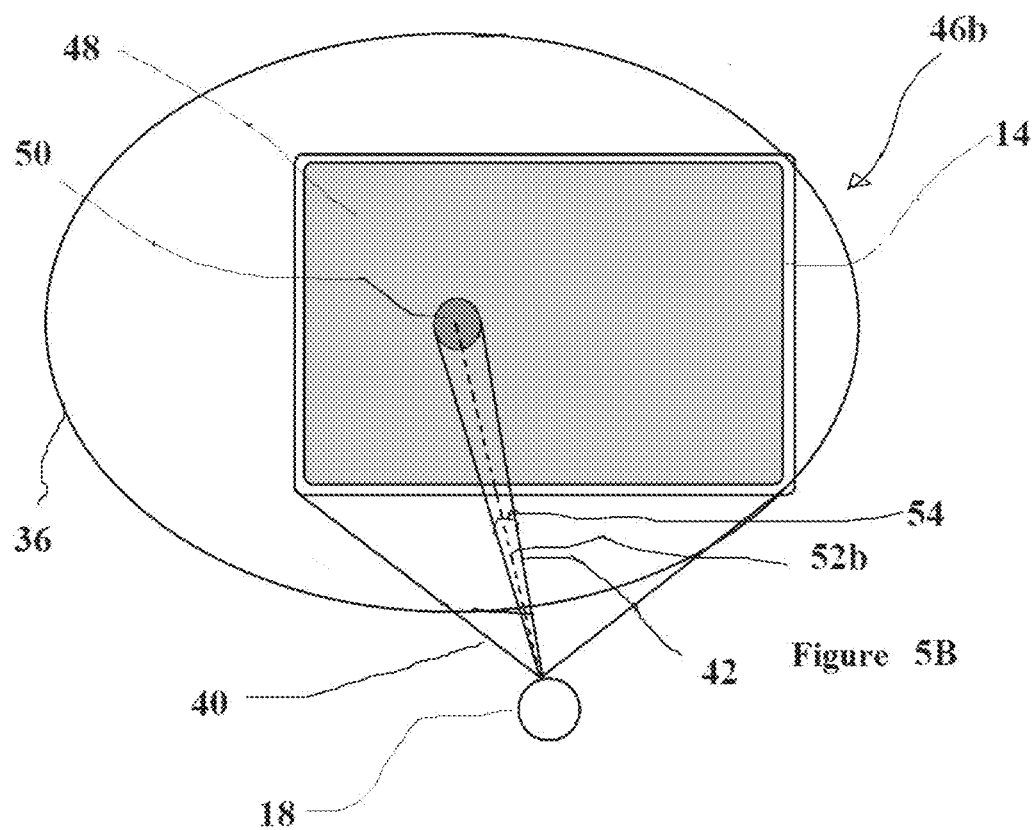
FIG. 5B is a schematic depiction of a display image or a second display image according to an embodiment of the teachings herein.

In FIG. 5B is depicted eye 18 (first eye or second eye) viewing an image 46b (a display image or a second display image) displayed on display screen 14 which also comprises two portions, a non-central vision portion 48 of image 46b which corresponds to a non-central portion 40 of field of view 36 of eye 18 and a central-vision portion 42 of image 46b which corresponds to a central portion 42 of field of view 36 of eye 18. For generation of image 46b from a base image, a gaze direction 52b was determined for eye 18 immediately prior to generation of image 46b, which gaze direction 52b was different from gaze direction 52a used for generating image 46a.

Central-Vision Portion of Display Image and Second Display Image

Position of Central-Vision Portion in Relation to Gaze Direction

As noted above, a central-vision portion of the display image corresponds to a portion of the field of view of the first eye that includes the determined gaze direction of the first eye and a central-vision portion of a second display image corresponds to a portion of the field of view of the second eye that includes the determined gaze direction of the second eye.

In some embodiments, the central-vision portion of the display image corresponds to a portion of the field of view of the first eye that is centered around the determined gaze direction of the first eye. Alternatively, in some embodiments, the central-vision portion of the display image corresponds to a portion of the field of view of the first eye that is not centered around the determined gaze direction of the first eye. Similarly, when applicable, in some embodiments, the central-vision portion of the second display image corresponds to a portion of the field of view of the second eye that is centered around the determined gaze direction of the second eye. Alternatively, in some embodiments, the central-vision portion of the second display image corresponds to a portion of the field of view of the second eye that is not centered around the determined gaze direction of the second eye.

In FIGS. 4A and 4B is indicated the angular dimensions 54 of a central portion 42 of field of view 36 of an eye of a subject.

In FIGS. 5A and 5B is seen how the dimensions of central-vision portion 42 of image 46a and of image 46b corresponds to the angular dimensions 54 of a central portion 42 of field of view 36 of eye 18. In FIGS. 5A and 5B, central-vision portions 42 of images 46a and 46b as well as central portions 42 of field of view 36 of eye 18 are centered around a respective gaze direction 52a or 52b.

Size of Central-Vision Portion

As known in the art, a normal human eye has multiple substantially concentric regions with different resolutions. In order of decreased resolution, the foveal field of view is about 2°, the central field of view is about 5°, the paracentral field of view is about 8°, the parafoveal field of view is about 10°, and the macular field of view is about 18°.

According to some embodiments of the teachings herein, the central-vision portion of the display image and/or second display image corresponds to a portion of the field of view of the respective eye that includes the gaze direction and has angular dimensions of not less than about 1° and not more than about 20°. On a display screen viewed from a 50 cm distance, a 1° angular dimension corresponds to about 0.88 cm and a 20° angular dimension corresponds to about 17.6 cm linear dimensions on the display screen.

Additionally or alternatively, in some preferred embodiments, the central-vision portion of the display image and/or second display image corresponds to a portion of the field of view of the respective eye that includes the gaze direction and has angular dimensions of not less than about 2°.

Additionally or alternatively, in some preferred embodiments, the central-vision portion of the display image and/or second display image corresponds to a portion of the field of view of the respective eye that includes the gaze direction and has angular dimensions of not more than about 16° not more than about 12°, not more than about 8° and even not more than about 5°.

According to some preferred embodiments of the teachings herein, the central-vision portion of the display image corresponds to a portion of the field of view of the first eye that includes the gaze direction and has angular dimensions of not less than about 2° and not more than about 8°. Similarly and when application, according to some preferred embodiments of the teachings herein, the central-vision portion of the second display image corresponds to a portion of the field of view of the second eye that includes the gaze direction and has angular dimensions of not less than about 2° and not more than about 8°. On a display screen viewed from a 50 cm distance, a 2° angular dimension corresponds to about 1.7 cm and a 8° angular dimension corresponds to about 7 cm linear dimensions on the display screen.

As known to a person having ordinary skill in the art and as noted immediately hereinabove, for given angular dimensions of a field of view, the physical size (e.g., in units of pixels and/or millimeters) of a corresponding second region of a corresponding display image and/or second display image is dependent on the distance between the cornea and the display screen. In some embodiments, the method further comprises: prior to the generating a display image 'b', providing the computer processor with a display screen to first-eye cornea distance; and the generating of the display image is also based on the provided display screen to first-eye cornea distance. Similarly, when applicable, in some embodiments, the method further comprises: prior to the generating a second display image 'e', providing the computer processor with a display screen to second-eye cornea distance; and the generating of the second display image is also based on the provided display screen to second-eye cornea distance. Specifically, the desired angular size of a central portion of a field of view of an eye is translated to physical dimensions of the central-vision portion of the display image or second display image on the display screen based on the received distance, for instance, using basic geometry. In some embodiments, the distance provided for generating the display image and the distance provided for generating the second display image is the same.

In some such embodiments, providing the computer processor with the display screen to first-eye and/or second-eye cornea distance comprises inputting a distance value or distance values as a parameter to the computer processor. In some embodiments, the display screen to cornea distance is known prior to implementation of the method and is fixed (e.g., when the display screen is a component of VR goggles). In preferred such embodiments, the display screen to cornea distance is provided to the computer processor as a stored parameter.

In some embodiments, the distance between the cornea and the display screen is not known a priori and/or can change during implementation of the method, e.g, when the display screen is of a computer, smartphone, tablet or television). In some such embodiments, an estimated "typical" display screen to cornea distance is provided to the computer processor as a stored parameter. For example, in some embodiments when the display screen is a display screen of a smartphone, the estimated distance is set at 30 cm. For example, in some embodiments when the display screen is a display screen of a tablet or a laptop/desktop computer, the estimated distance is set at 45 cm. For example, in some embodiments when the display screen is display screen of a television, the estimated distance is set in accordance with and ideal viewing distance to screen size. For example, some people having ordinary skill in the art consider ideal viewing distance to typical screen sizes as follows: 32" screen ideally viewed from 1.37 m, 40" screen ideally viewed from 1.62 m, 50" screen ideally viewed from 2.13 m, 60" screen ideally viewed from 2.56 m, 70" screen ideally viewed from 2.99 m, and 80" screen ideally viewed from 3.41 m.

In some alternative embodiments, where the distance between the cornea and the display screen is not known a priori and/or can change during implementation of the method, the actual distance is determined and then provided to the computer processor. Accordingly, in some such embodiments providing the computer processor with the display screen to first-eye cornea distance comprises determining a distance between the display screen and a cornea of the first eye of the subject, which determined distance is used to generate the display image and, in some embodiments, also the second display image. Similarly, when applicable, in some embodiments providing the computer processor with the display screen to second-eye cornea distance comprises determining a distance between the display screen and a cornea of the second eye of the subject, which determined distance is used to generate the second display image. Determining such a distance can be done in any suitable manner using any suitable device or combination of devices. In some embodiments, the distance is determined using a dedicated range finder (e.g. using a commercially-available IR range finder or ultrasonic range finder). Additionally or alternatively, in some embodiments where the display screen is functionally associated with a camera (as is typical for smartphones, tablets, laptop computers, many desktop computers, some television displays), the determining the distance is determined from analysis of an image acquired of a person viewing the screen. For example, when the devices depicted in FIG. 1 and FIG. 3 are configured to determine a display screen to cornea distance, this is preferably performed using a camera built into the frame of displays screen 14 which is not depicted. Typically in such embodiments, there is a set-up procedure where the human subject for which the method is to be implemented views the screen at one or more pre-determined distances. At each one of the one or more pre-determined distances, a reference image is acquired. The size of one or more features or distance between features such as the head or eyes in the reference image or images is correlated with the corresponding pre-determined distance to be used as reference values to determine the display screen to cornea distance during actual implementation of the method.

Shape of Central-Vision Portion

The shape of the central-vision portion of the display image and/or second display image on a display screen is any suitable shape. In some embodiments, the shape of the central-vision portion on a display screen is a circle (as depicted in FIGS. 5A and 5B). Alternatively, in some embodiments the shape of the central-vision portion of the display image and/or second display image is a shape different from a circle, e.g., is oval, square, or rectangle. In preferred such embodiments, the smallest dimension of the central-vision portion corresponds to angular dimensions of not less than about 1° and the largest dimension of the central-vision portion corresponds to an angular dimension of not more than about 20°.

The shape of the central-vision portion in some embodiments is discussed in greater detail hereinbelow.

Modification to the Central-Vision Portion of an Image

As noted above, the central-vision portion of the display image is either unmodified compared to a corresponding portion in the base image; or modified so that visual characteristics of the central-vision portion of the display image are changed compared to corresponding visual characteristics of a corresponding portion in the base image which modification improves the image quality of the central-vision portion relative to the corresponding portion in the base image. Similarly, when applicable the central-vision portion of the second display image is either unmodified compared to a corresponding portion in the base image; or modified so that visual characteristics of the central-vision portion of the second display image are changed compared to corresponding visual characteristics of a corresponding portion in the base image which modification improves the image quality of the central-vision portion relative to the corresponding portion in the base image.

In some embodiments, the central-vision portion is unmodified compared to the corresponding portion in the base image, that is to say, the central-vision portion is the same as the corresponding portion of the base image: what the eye perceives in the central portion of the field of view when viewing the display image or the second display image is the same as if the eye viewed the base image.

Alternatively, in some embodiments, the central-vision portion of the display image is modified so that visual characteristics of the central-vision portion of the display image are changed compared to corresponding visual characteristics of a corresponding portion in the base image which modification improves the image quality of the central-vision portion relative to the corresponding portion in the base image. Similarly, when applicable in some embodiments the central-vision portion of the second display image is modified so that visual characteristics of the central-vision portion of the second display image are changed compared to corresponding visual characteristics of a corresponding portion in the base image which modification improves the image quality of the central-vision portion relative to the corresponding portion in the base image. Modifications that improve image quality are any suitable modifications known in the art of image processing. In some embodiments, such modifications includes applying at least one image processing method to the corresponding portion of the base image selected from the group consisting of increasing contrast, sharpening, changing the brightness, changing color and combinations thereof.

As known in the art, in some instances a human subject has asymmetric vision, that is to say, has visual deficiencies that cause the two eyes perceiving the same viewed image differently. In some preferred embodiments that include generating both a display image and a second display image, the modification to the central-vision portion of the base image includes "balancing" the central-vision portion of the display image with the central-vision portion of the second display image so that these are perceived by the respective eyes as being more similar and even identical. Accordingly, in some embodiments wherein the subject has an asymmetric vision defect so that the left eye and the right eye perceive an identical viewed image differently, and wherein the modifying a portion of the base image corresponding to the central-vision portion of the display image and the modifying a portion of the base image corresponding to the central-vision portion of the second display image together comprise compensating for the asymmetric vision defects so that the central-vision portion of the display image and the central-vision portion of the second display image are perceived more similar than without such modifying. In such embodiments, the modifying of the corresponding portion of the base images to generate the central-vision portion of the display image and/or second display image comprises at least one image processing method selected from the group consisting of:

changing the size (magnifying/reducing) of the central-vision portion of the base image to yield a central-vision portion of the display image and/or the second display image;

changing the blurring and/or sharpening of the central-vision portion of the base image to yield a central-vision portion of the display image and/or the second display image;

changing the brightness (increasing/decreasing) of the central-vision portion of the base image to yield a central-vision portion of the display image and/or the second display image; and changing the contrast (increasing/decreasing) of the central-vision portion of the base image to yield a central-vision portion of the display image and/or the second display image.

Alternatively, in some embodiments the central-vision portion of the display image is modified so that visual characteristics of the central-vision portion of the display image are changed compared to corresponding visual characteristics of a corresponding portion in the base image which modification changes the image quality of the central-vision portion relative to the corresponding portion in the base image. In some embodiments, such modification improves the image quality of the central-vision portion of the display image relative to the corresponding portion in the base image. Similarly, in some embodiments the central-vision portion of the second display image is modified so that visual characteristics of the central-vision portion of the display image are changed compared to corresponding visual characteristics of a corresponding portion in the base image which modification changes the image quality of the central-vision portion relative to the corresponding portion in the base image. In some embodiments, such modification improves the image quality of the central-vision portion of the second display image relative to the corresponding portion in the base image.

Non-Central Vision Portion of Display Image/Non-Central Portion of Field of View As noted above, in some embodiments a display image is generated from a received digital base image wherein a non-central vision portion of the display image that is different from the central-vision portion is either: unmodified compared to a corresponding portion in the base image; or modified so that visual characteristics of the non-central vision portion of the display image are changed compared to corresponding visual characteristics of a corresponding portion in the base image, wherein as a result of the generating, an image quality of the non-central vision portion of the display image is lower than the image quality of the central-vision portion of the display image. Similarly, when relevant a second display image is generated from a received digital base image wherein a non-central vision portion of the second display image that is different from the central-vision portion is either: unmodified compared to a corresponding portion in the base image; or modified so that visual characteristics of the non-central vision portion of the second display image are changed compared to corresponding visual characteristics of a corresponding portion in the base image, wherein as a result of the generating, an image quality of the non-central vision portion of the second display image is lower than the image quality of the central-vision portion of the second display image.

The relative orientation of the central vision portion and the non-central vision portion in the display image and/or second display image is any suitable relative orientation. In some embodiments, the non-central vision portion is contiguous with the central vision portion. In some embodiments, the non-central vision portion of the display image at least partially surrounds the central vision portion. In some embodiments, the non-central vision portion of the display image completely surrounds the central-vision portion. In FIGS. 5A and 5B, the non-central vision portion 48 of images 46a and 46b are contiguous with and completely surround the central-vision portion 50 of the images.

The size of the non-central vision portion of a display image and second display image is any suitable size. In some embodiments, the radial dimensions of the non-central vision portion of the display image corresponds to a field of view of the first eye of at least about 2°. Similarly and when applicable, in some embodiments the radial dimensions of the non-central vision portion of the second display image corresponds to a field of view of the first eye of at least about 2°.

In some embodiments, the non-central vision portion is at least 1% of the area of the display image that is not the central-vision portion, for example, constituting a thin ring surrounding the central-vision portion. Similarly and when applicable, in some embodiments, the non-central vision portion is at least 1% of the area of the second display image that is not the central-vision portion. In some preferred embodiments, the non-central vision portion of the display image and/or the second display image is at least about 30% of the area of the display image that is not the central-vision portion. In some preferred embodiments, the non-central vision portion of the display image and/or the second display image is at least about 40%, at least about 50%, at least about 60%, at least about 70% at least about 80%, at least about 90%, at least about 95% and even about 100% of the area of the display image/second display image that is not the central-vision portion. In FIGS. 5A and 5B, non-central vision portion 48 of images 46a and 46b is 100% of the area of the images that is not the central-vision portion 48.

The shape of the non-central portion of a display image and/or second display image is any suitable shape, in some embodiments a shape selected from the group consisting of a circle, an oval, a polygon, a square and a rectangle.

In some embodiments, the non-central vision portion of the display image is unmodified compared to a corresponding portion in the base image. Similarly, when applicable, in some the non-central vision portion of the second display image is unmodified compared to a corresponding portion in the base image.

In some preferred embodiments the non-central vision portion of the display image is modified so that visual characteristics of the non-central vision portion of the display image are changed compared to corresponding visual characteristics of a corresponding portion in the base image which modification changes the image quality of the non-central vision portion of the display image relative to the corresponding portion in the base image. In some embodiments, such modification improves the image quality of the non-central vision portion of the display image relative to the corresponding portion in the base image. In some preferred embodiments, such modification degrades the image quality of the non-central vision portion of the display image relative to the corresponding portion in the base image. Similarly, when applicable, in some preferred embodiments the non-central vision portion of the second display image is modified so that visual characteristics of the non-central vision portion of the second display image are changed compared to corresponding visual characteristics of a corresponding portion in the base image which modification changes the image quality of the non-central vision portion of the second display image relative to the corresponding portion in the base image. In some embodiments, such modification improves the image quality of the non-central vision portion of the second display image relative to the corresponding portion in the base image.

In some embodiments, the modification which degrades the image quality of the non-central vision portion of the display image and/or of the second display image relative to the corresponding portion in the base image includes at least one member selected from the group consisting of:

reduced resolution compared to the corresponding portion of the base image;

blurring compared to the corresponding portion of the base image;

reduced contrast compared to the corresponding portion of the base image;

reduced/increased brightness compared to the corresponding portion of the base image;

reduced color intensity compared to the corresponding portion of the base image;

changed or reduced color palette compared to the corresponding portion of the base image;

and combinations thereof.

In preferred embodiments, the modification which degrades the image quality of the non-central vision portion of the display image and/or the second display image relative to the corresponding portion in the base image includes at least one member selected from the group consisting of: reduced resolution; blurring; reduced contrast and combinations thereof.

In some embodiments, the changes to the visual characteristics of the non-central vision portion of the display image are homogeneous, that is to say, the type and degree of modification is identical for the entire non-central vision portion. Similarly, when applicable, in some embodiments, the changes to the visual characteristics of the non-central vision portion of the second display image are homogeneous.

Alternatively, in some embodiments, the changes to the visual characteristics of the non-central vision portion of the display image are not-homogeneous that is to say, the type and degree of modification is not identical for the entire non-central vision portion. Similarly, when applicable, in some embodiments, the changes to the visual characteristics of the non-central vision portion of the second display image are not homogeneous. For example, in some embodiments, the modification is a gradient where the degree of modification is increasingly greater closer to the central-vision portion. Alternatively and more preferably, in some such embodiments, the modification is a gradient where the degree of modification is increasingly greater further from the central-vision portion. Additionally or alternatively, in some embodiments the non-central vision portion has n distinct parts, n being an integer greater than one, each distinct part having a different modification. For example, in some embodiments, the central-vision portion includes two annular parts, an inner annular part with a first type of modification and an outer annular part of with a second type of modification different from the first type of modification and/or where the inner annular part has a first degree of modification and an outer annular part of has a second degree of modification different from the first degree of modification.

The degree of degradation is any suitable degree of degradation. In some embodiments, the degree of degradation is changed during the course of treatment, for example, in response to how the treatment treats a specific subject. For example, the vision of a subject being treated is typically monitored at intervals of between 3 and 6 months. If a monitoring session of a subject shows that the refractive errors have significantly worsened during a preceding treatment period, the degree of degradation is increased for the subsequent treatment period. In contrast, if a monitoring session of a subject shows that the refractive errors have kept stable or mildly worsened, during a preceding treatment period, the degree of degradation is kept the same or decreased for the subsequent treatment period.

The initial degree of degradation is any suitable degree of degradation and can be determined in any suitable way, typically based on the experience of a person, such as an ophthalmologist. In some embodiments, the subject is shown a regular image which is degraded to some degree using some type of modification. When the subject indicates that a specific degradation is such that it makes it difficult to perceive previously-apparent details in the image, that specific degradation is taken as an initial degree of degradation.

In FIGS. 6A-6K are depicted various embodiments of display images 46 displayed on a display screen 14, each display image 46 having a central-vision portion 50 and a non-central vision portion 48. In FIGS. 6, a gaze direction 52 of an eye 18 used for generating display images 46 is also depicted.

Figure 6A:
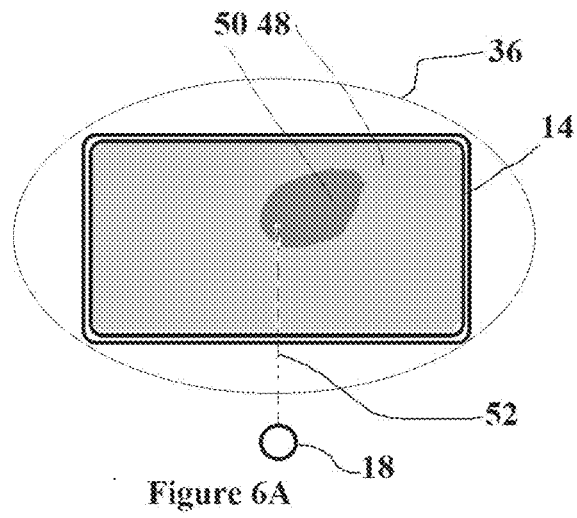
FIGS. 6A-6K schematically depict different embodiments of a display image which can also be considered second display images, and can also be considered to display different embodiments of mask images.

In FIG. 6A, central-vision portion 50 is not a circle and not centered around gaze direction 52, but is elongated towards the upper right part of display screen 14. Non-central vision portion 48 completely surrounds central vision portion 50 and makes up 100% of the surface area of display screen 14 that is not covered by central vision portion 50.

Figure 6B:
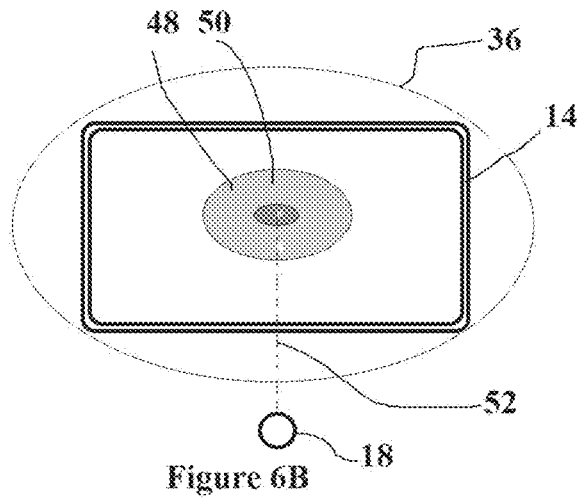

In FIG. 6B, central-vision portion 50 is an oval centered-around gaze direction 52 and is completely surrounded by non-central vision portion 48 which is shaped like an oval ring and makes up about 10% of the surface area of display screen 14 that is not covered by central vision portion 50.

Figure 6C:
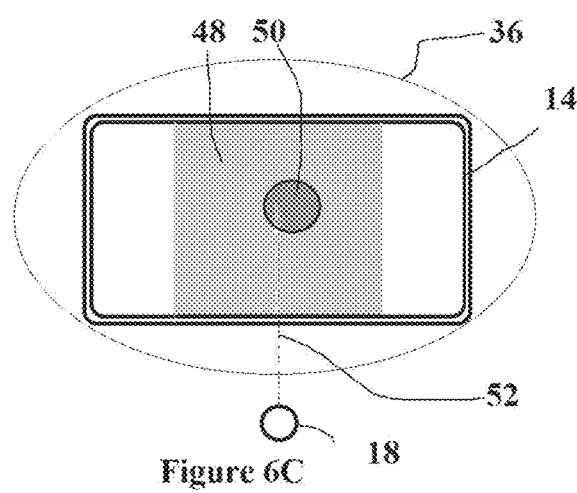

In FIG. 6C, central-vision portion 50 is a circle, is not centered-around gaze direction 52 and is completely surrounded by non-central vision portion 48. Non-central vision portion 48 makes up about 50% of the surface area of display screen 14 that is not covered by central vision portion 50.

Figure 6D:
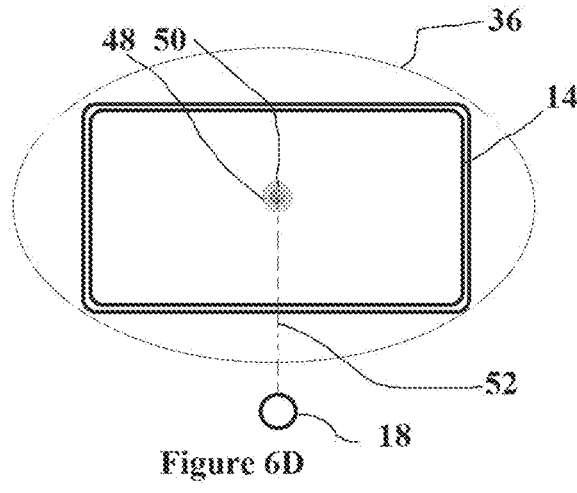

In FIG. 6D, central-vision portion 50 is a circle, centered-around gaze direction 52 and is completely surrounded by non-central vision portion 48. Non-central vision portion 48 is a ring and makes up about 2% of the surface area of display screen 14 that is not covered by central vision portion 50.

Figure 6E:
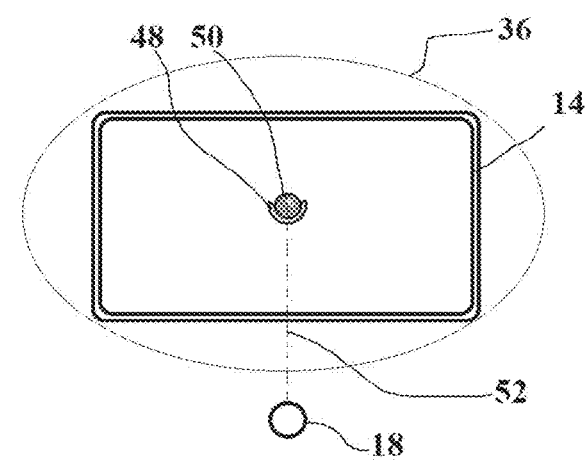

In FIG. 6E, central-vision portion 50 is a circle, centered-around gaze direction 52 and is partially surrounded by non-central vision portion 48. Non-central vision portion 48 is a 190° arc and makes up about 2% of the surface area of display screen 14 that is not covered by central vision portion 50.

Figure 6F:
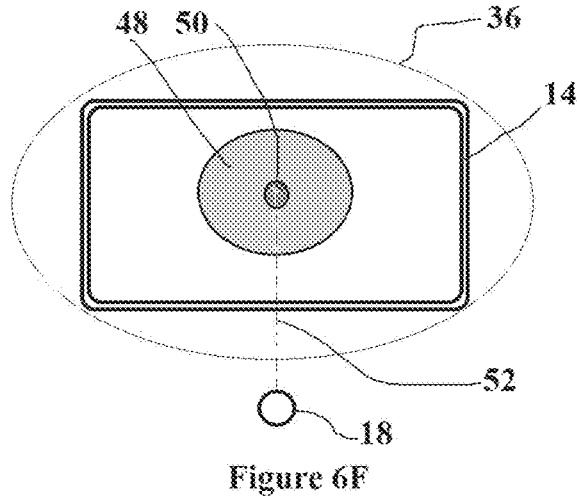

In FIG. 6F, central-vision portion 50 is a circle, centered-around gaze direction 52 and is completely surrounded by non-central vision portion 48. Non-central vision portion 48 is an oval-shaped ring and makes up about 20% of the surface area of display screen 14 that is not covered by central vision portion 50.

Figure 6G:
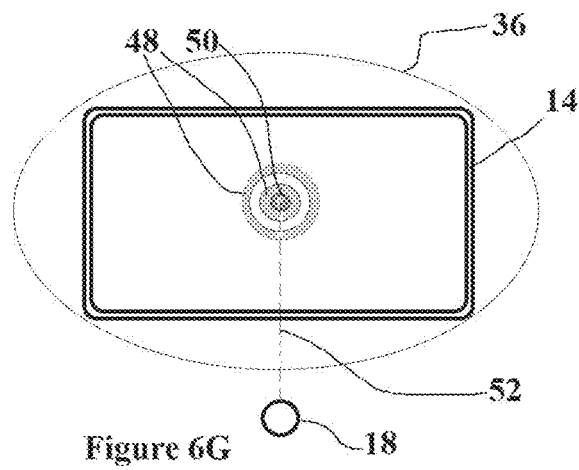

In FIG. 6G, central-vision portion 50 is a circle, centered-around gaze direction 52 and is completely surrounded by non-central vision portion 48. Non-central vision portion 48 is two physically-separated rings, concentric with central vision portion 50, an inner ring that is contiguous with central-vision portion 50 and an outer ring.

Figure 6H:
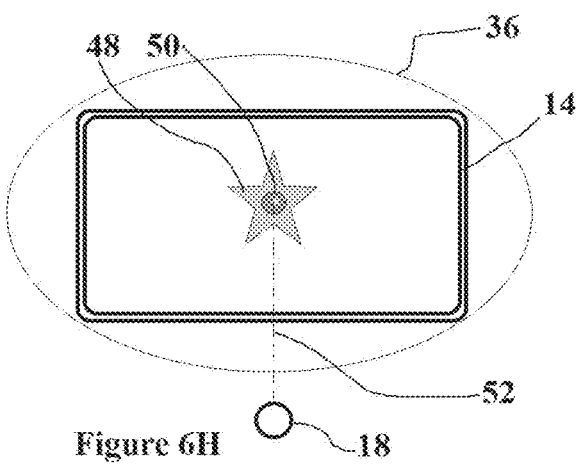

In FIG. 6H, central-vision portion 50 is a circle, centered-around gaze direction 52 and is completely surrounded by non-central vision portion 48. Non-central vision portion 48 is star-shaped and makes up about 5% of the surface area of display screen 14 that is not covered by central vision portion 50.

Figure 6I:
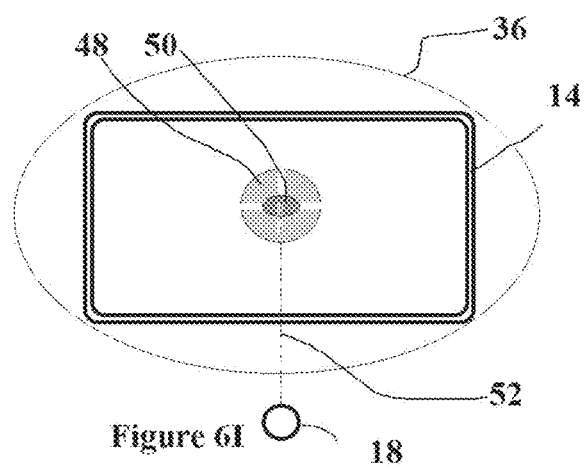

In FIG. 6I, central-vision portion 50 is oval-shaped, centered-around gaze direction 52 and is partially surrounded by non-central vision portion 48. Non-central vision portion 48 is a discontinuous ring made up of four separate truncated pie shapes.

Figure 6J:
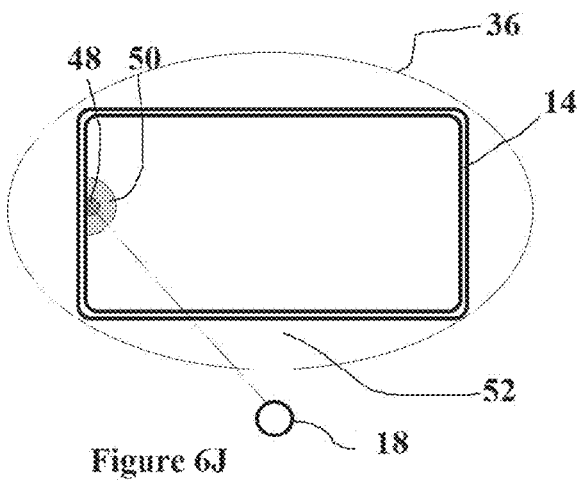

In FIG. 6J is depicted a situation where the gaze direction 18 is close to the edge of screen 14. As a result, central-vision portion 50 is truncated circle which, if not truncated, would be centered-around gaze direction 52. Non-central vision portion 48 is a truncated ring-shape which partially surrounds central vision portion 50 due to the truncation.

Figure 6K:
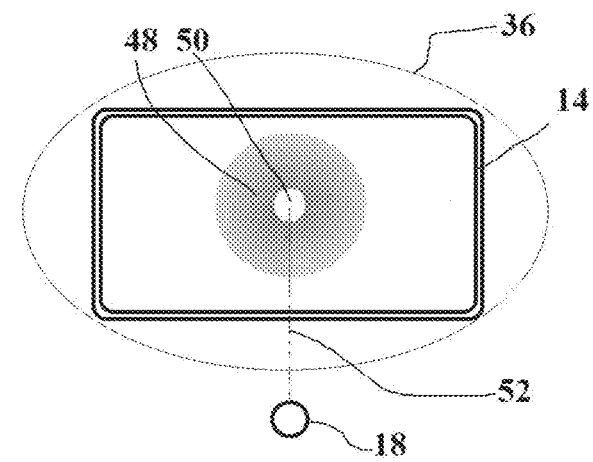

In FIG. 6K, central-vision portion 50 is a circle, centered-around gaze direction 52 and is completely surrounded by non-central vision portion 48. Non-central vision portion 48 is a circular ring shape and makes up about 20% of the surface area of display screen 14 that is not covered by central vision portion 50. The level of degradation of non-central vision portion 48 is a gradient, where degradation is greater then closer to central vision portion 50.

It is important to note, that the component labeled 46 in FIGS. 6A-6K is a display image but, in relevant embodiments, also represents a second display image. Further, the component labeled 46 in FIGS. 6A-6K can also be considered to represent a mask image in suitable embodiments.

Figure 7A:
FIG. 7A schematically depicts a base image.
Figure 7B:
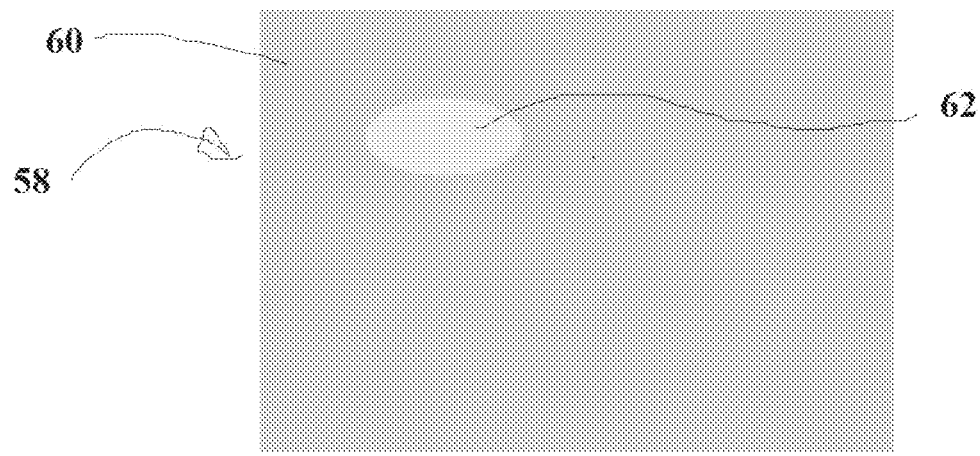
FIG. 7B schematically depicts a mask image.
Figure 7C:
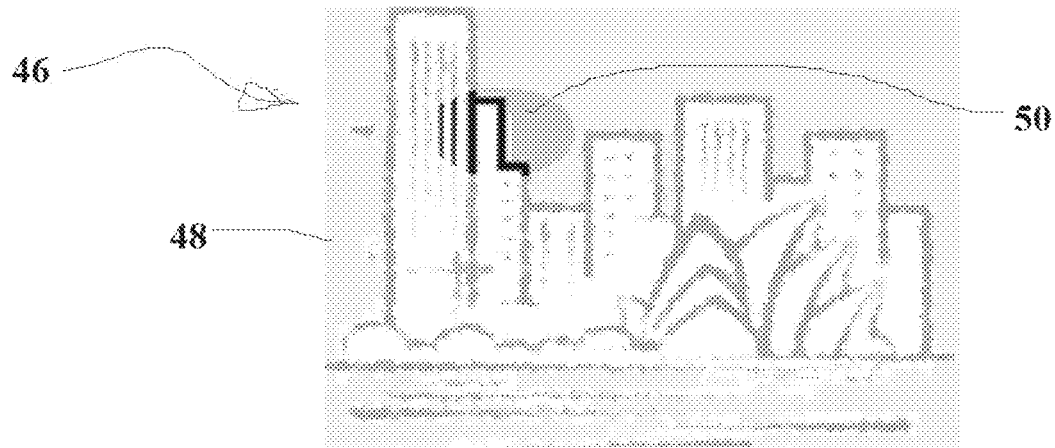
FIG. 7C schematically depicts a display image derived from the base image of FIG. 7A and the mask image of FIG. 7B.

In FIGS. 7A, 7B and 7C is schematically depicted a base image 56 in FIG. 7A, a mask image 58 and a display image 46 that is generated and displayed when base image 56 and mask image 58 are displayed together on a display screen. In FIG. 7B, a degrading non-central vision portion 60 and a non-degrading central-vision portion 62 are indicated for mask image 58. In FIG. 7C, a central-vision portion 50 and a non-central vision portion 48 of display image 46 are indicated.

Determining the Gaze Direction of an Eye of the Subject

As noted above, a method according to the teachings herein includes determining the gaze direction of one or both eye of the subject and then generating a display image and/or a second display image based on the determined gaze direction or directions.

The gaze direction of one or both eyes is determined in any suitable way, in some preferred embodiments using an eye tracker. In the devices depicted in FIGS. 1 and 3, the gaze direction of both eyes 18a and 18b is determined using eye tracker 16.

The display image that is generated based on a determined gaze direction of a first eye is such that the gaze direction of the first eye passes through the central-vision portion of the display image. In whatever direction the first eye moves relative to the display screen on which the display image is displayed, the display image is generated so that the gaze direction of the first eye passes through the central-vision portion.

When applicable, the second display image that is generated based on a determined gaze direction of a second eye is such that the gaze direction of the second eye passes through the central-vision portion of the second display image. In whatever direction the second eye moves relative to the display screen on which the second display image is displayed, the second display image is generated so that the gaze direction of the second eye passes through the central-vision portion.

Pupil Size and Pupil-Size Determiner

In some embodiments, the size and/or shape and/or the degree of a modification and/or the type of modification of a base image to generate a central-vision portion or a non-central vision portion of a display image is dependent also on a determined pupil size of the first eye. Similarly, and when applicable, in some embodiments, the size and/or shape and/or the degree of a modification and/or the type of modification of a base image to generate a central-vision portion or a non-central vision portion of a second display image is dependent also on a determined pupil size of the second eye.

Accordingly, in some embodiments, the method further comprises, prior to the generating of a display image 'b', providing the computer processor with a size of the pupil of the first eye; and generating the display image is also based on the provided size of the pupil of the first eye. Additionally or alternatively, in some embodiments, the method further comprises, prior to the generating of a second display image 'e', providing the computer processor with a size of the pupil of the second eye; and generating the second display image is also based on the provided size of the pupil of the second eye.

The size of a pupil can be determined in any suitable way using an suitable device or combination of devices. For example, in the art, the use of an eye tracker to determine a pupil size is well known.

Pupil Size

In some embodiments, for any two different generated display images, the non-central vision portion of the display image generated when a larger pupil size is detected and provided to the computer processor is modified to a lesser degree (preferably degraded to a lesser degree) than the non-central vision portion of the display image generated when a smaller pupil size is detected and provided to the computer processor. Similarly, in some embodiments, for any two different generated second display images, the non-central vision portion of the second display image generated when a larger pupil size is detected and provided to the computer processor is modified to a lesser degree (preferably degraded to a lesser degree) than the non-central vision portion of the second display image generated when a smaller pupil size is detected and provided to the computer processor.

In some embodiments, for any two different generated display images, the central-vision portion of the display image generated when a larger pupil size is detected and provided to the computer processor is larger than the non-central vision portion of the display image generated when a smaller pupil size is detected and provided to the computer processor. In some embodiments, for any two different generated second display images, the central-vision portion of the second display image generated when a larger pupil size is detected and provided to the computer processor is larger than the non-central vision portion of the second display image generated when a smaller pupil size is detected and provided to the computer processor.

In some embodiments of the device, the device is configured for determining the size of the pupil of the first eye of a subject viewing the display screen and providing the determined pupil size to the computer processor, and the computer processor is further configured to generate a display image and/or a second display image also based on the determined first-eye pupil size, for example, as discussed above. In some embodiments of the device, the device is configured for determining the size of the pupil of the first eye and/or of the pupil of the second eye of a subject viewing the display screen and providing the determined pupil sizes to the computer processor, and the computer processor is further configured to generate a display image also based on the determined first-eye pupil size and to generate a second display image also based on the determined second-eye pupil size. Components that can be associated with such a device for determining the size of the pupils of one or both eyes are well known and include one or more cameras and some types of eye trackers, for example, as discussed above.

Compensation for Eye Movement

Generally speaking, during a given session where a subject is viewing a display screen according to the teachings herein, the central-vision portion of a display image or second display image is viewed by the central vision of a respective eye while the non-central vision portion of a display image or second display image is viewed by more peripheral vision of the respective eye.

When the determining of gaze direction, generating of an image and display of a generated image is sufficiently fast (e.g., faster than 60 Hz), the person or subject viewing the display screen or screens may not be aware of the modifications made to the viewed image.

It has been found that in some instances, particularly when the teachings are implemented using weaker computer processors or with more complex image processing algorithms applied to a base image to generate a display image, the delay between determining the gaze direction and displaying a generated image allows the foveal vision to perceive the non-central vision portion of a generated image being displayed which can cause discomfort or irritation, especially when the non-central vision portion is degraded.

To overcome this, in some embodiments the method further comprises:

monitoring the speed and amplitude of the movement of the first eye and, if the speed and amplitude of movement of the first eye is greater than specified thresholds, then not displaying (and even not generating) a display image and/or a second display image, in some embodiments displaying the base image instead. The thresholds are typically set according to the properties of the specific hardware.

In some embodiments the method further comprises determining the motion vector of the gaze direction of the first eye and, if the determined motion vector of the gaze direction of the first eye is larger that a threshold then the computer processor generating a display image and/or second display image also based on the determined motion vector. The display image and/or second display image is generated such that the central-vision portion is sufficiently large and of the correct shape so that the viewer is less likely to perceive the non-central vision portion of a generated image being displayed with foveal vision. In some such embodiments, a larger motion vector leads to generation of a larger central-vision portion. Additionally or alternatively, in some such embodiments, a larger motion vector leads to generation of a central-vision portion having an elongated shape having small dimensions perpendicular to the determined motion vector and larger dimensions parallel to the determined motion vector. Similarly, and when applicable, in some embodiments the method further comprises determining the motion vector of the gaze direction of the second eye and, if the determined motion vector of the gaze direction of the second eye is larger that a threshold then the computer processor generating a display image also based on the determined motion vector. The second display image is generated such that the central-vision portion is sufficiently large and of the correct shape so that the viewer is less likely to perceive the non-central vision portion of a generated second display image being displayed with foveal vision. In some such embodiments, a larger motion vector leads to generation of a larger central-vision portion. Additionally or alternatively, in some such embodiments, a larger motion vector leads to generation of a central-vision portion having an elongated shape having small dimensions perpendicular to the determined motion vector and larger dimensions parallel to the determined motion vector.

Unless otherwise defined, all technical and scientific terms used herein have the same meaning as commonly understood by one of ordinary skill in the art to which the invention pertains. In case of conflict, the specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof.

As used herein, the indefinite articles "a" and "an" mean "at least one" or "one or more" unless the context clearly dictates otherwise.

As used herein, when a numerical value is preceded by the term "about", the term "about" is intended to indicate +/−10%.

As used herein, a phrase in the form "A and/or B" means a selection from the group consisting of (A), (B) or (A and B). As used herein, a phrase in the form "at least one of A, B and C" means a selection from the group consisting of (A), (B), (C), (A and B), (A and C), (B and C) or (A and B and C).

Embodiments of methods and/or devices described herein may involve performing or completing selected tasks manually, automatically, or a combination thereof. Some methods and/or devices described herein are implemented with the use of components that comprise hardware, software, firmware or combinations thereof. In some embodiments, some components are general-purpose components such as general purpose computers or digital processors. In some embodiments, some components are dedicated or custom components such as circuits, integrated circuits or software.

For example, in some embodiments, some of an embodiment is implemented as a plurality of software instructions executed by a data processor, for example which is part of a general-purpose or custom computer. In some embodiments, the data processor or computer comprises volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more of input devices (e.g., allowing input of commands and/or parameters) and output devices (e.g., allowing reporting parameters of operation and results).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

What is claimed is:

1. A method useful for the treatment of existing refractive errors and/or prevention of the development of refractive errors in a human subject, comprising:
   a. determining a gaze direction of a first eye of a subject viewing an image on a display screen and providing said determined gaze direction to a computer processor;
   b. subsequent to 'a', based on said determined gaze direction of the first eye, with a computer processor generating a display image for display to the first eye on said display screen from a received digital base image, wherein:
      i. a central-vision portion of said display image that corresponds to a portion of the field of view of the first eye that includes said determined gaze direction, wherein the central-vision portion is either:
      unmodified compared to a corresponding portion in said base image; or
      modified so that visual characteristics of said central-vision portion of said display image are changed compared to corresponding visual characteristics of a corresponding portion in said base image which modification improves the image quality of said central-vision portion relative to the corresponding portion in said base image, and
      ii. a non-central vision portion of said display image that is different from said central-vision portion is either:
      unmodified compared to a corresponding portion in said base image; or
      modified so that visual characteristics of said noncentral vision portion of said display image are changed compared to corresponding visual characteristics of a corresponding portion in said base image,
   wherein as a result of said generating, an image quality of said non-central vision portion of said display image is lower than the image quality of said central-vision portion of said display image; and
   c. displaying said generated display image on said display screen so that the first eye of the subject views said display image on said display screen, wherein said non-central portion of said display image is modified so that visual characteristics of said non-central vision portion of said display image are changed compared to corresponding visual characteristics of a corresponding portion in said base image which modification degrades the image quality of said non-central vision portion relative to the corresponding portion in said base image, wherein said modification which degrades the image quality of said non-central vision portion relative to the corresponding portion in said base image includes at least reduced contrast.

2. The method of claim 1, further comprising: displaying said generated display image on a display screen so that the second eye of the subject views said display image on a display screen.

3. The method of claim 2, wherein said display image is displayed at a same location of said display screen for both eyes to view simultaneously.

4. The method of claim 1, further comprising, concurrently with 'a' and 'b':
   d. determining a gaze direction of a second eye of the subject viewing a second eye display screen and providing said determined gaze direction to a computer processor;
   e. subsequent to 'c', based on said determined gaze direction of the second eye, with a computer processor generating a second display image for display to the second eye on said second eye display screen from said received digital base image, wherein:
      i. a central-vision portion of said second display image that corresponds to a portion of the field of view of the second eye that includes said determined gaze direction is either:
      unmodified compared to a corresponding portion in said base image; or
      modified so that visual characteristics of said central-vision portion of said second display image are changed compared to corresponding visual characteristics of a corresponding portion in said base image which modification improves the image quality of said central-vision portion relative to the corresponding portion in said base image, and
      ii. a non-central vision portion of said second display image that is different from said central-vision portion is either:
      unmodified compared to a corresponding portion in said base image; or
      modified so that visual characteristics of said noncentral vision portion of said second display image are changed compared to corresponding visual characteristics of a corresponding portion in said base image,
   wherein as a result of said generating, an image quality of said non-central vision portion of said second display image is lower than the image quality of said central-vision portion of said second display image; and
   f. displaying said generated second display image on said second eye display screen so that the second eye of the subject views said second display image on said second eye display screen, wherein said non-central portion of said second display image is modified so that visual characteristics of said non-central vision portion of said second display image are changed compared to corresponding visual characteristics of a corresponding portion in said base image which modification degrades the image quality of said non-central vision portion relative to the corresponding portion in said base image, wherein said modification which degrades the image quality of said non-central vision portion relative to the corresponding portion in said base image includes at least reduced contrast.

5. The method of claim 1, wherein a size of said central-vision portion of said display image corresponds to a field of view of the first eye of at least about 1° and not more than about 20° that includes said determined gaze direction of the first eye.

6. The method of claim 1, wherein said central-vision portion of said display image is unmodified compared to a corresponding portion in said base image.

7. The method of claim 1, wherein said central-vision portion of said display image is modified so that visual characteristics of said central-vision portion of said display image are changed compared to corresponding visual characteristics of a corresponding portion in said base image which modification improves the image quality of said central-vision portion relative to the corresponding portion in said base image.

8. The method of claim 1, wherein said non-central vision portion of said display image completely surrounds said central-vision portion.

9. The method of claim 1, wherein a radial dimensions of said noncentral vision portion of said display image corresponds to a field of view of the first eye of at least about 2°.

10. The method of claim 1, wherein said generating said display image comprises generating said display image as an image data structure and said displaying of said generated display image is subsequently displaying of said image data structure on said display screen.

11. The method of claim 1, wherein said generating said display image comprises:
generating a mask image which is non-dependent on the base image comprising a non-degrading central vision portion and a degrading non-central vision portion; and
subsequently displaying said mask image together with said base image on said display screen so as to concurrently generate and display said display image.

12. The method of claim 1, further comprising, prior to said generating a display image 'b', providing said computer processor with a display screen to first-eye cornea distance; and said generating said display image is also based on said provided display screen to first-eye cornea distance.

13. The method of claim 11, wherein said displaying said generated mask image together with said base image does not effect the appearance of the central vision portion of the base image on said display screen so that the portions of the base image corresponding to the central-vision portion appear to a subject to be unmodified.

14. The method of claim 11, wherein said displaying said generated mask image together with said base image changes the appearance of the noncentral vision portion of the base image on the display screen, so that the portions of the base image corresponding to the non-central vision portion appear to a subject to be degraded.

15. A device for image processing and display, comprising:
a computer processor functionally associated with a display screen and an eye tracker, said eye tracker configured for determining a gaze direction of a first eye of a person viewing an image on said display screen and for providing a determined gaze direction to said computer processor said computer processor configured:
to generate a display image from a received digital base image based on a gaze direction of the first eye received from said eye tracker, wherein:
  i. a central-vision portion of said display image that corresponds to a portion of the field of view of the first eye that includes said determined gaze direction, wherein the central-vision portion is either:
    unmodified compared to a corresponding portion in said base image; or
    modified so that visual characteristics of said central vision portion of said display image are changed compared to corresponding visual characteristics of a corresponding portion in said base image which modification improves the image quality of said central-vision portion relative to the corresponding portion in said base image, and
  ii. a non-central vision portion of said display image that is different from said central-vision portion is either:
    unmodified compared to a corresponding portion in said base image; or
    modified so that visual characteristics of said noncentral vision portion of said display image are changed compared to corresponding visual characteristics of a corresponding portion in said base image,
wherein as a result of said generating, an image quality of said non-central vision portion of said display image is lower than the image quality of said central-vision portion of said display image; and
to display said generated display image on said display screen so that the first eye of the person views said display image on said display screen, wherein said computer processor is configured to modify a base image so that visual characteristics of a non-central portion of a generated display image are changed compared to corresponding visual characteristics of a corresponding portion in the base image which modification degrades the image quality of the non-central vision portion relative to the corresponding portion in the base image, wherein said modification which degrades the image quality of a non-central vision portion of a display image relative to the corresponding portion in a base image includes at reduced contrast.

16. The device of claim 15, said display screen configured so that the second eye of the person can view a generated display image on a display screen.

17. The device of claim 16, wherein a generated display image is displayed at a same location of said display screen for both eyes to view simultaneously.

18. The device of claim 15, further comprising,
an eye tracker configured for determining a gaze direction of a second eye of a person viewing said display screen and for providing a determined gaze direction to said computer processor;
said computer processor further configured:
to generate a second display image from a received digital base image and based on a gaze direction of the second eye received from said eye tracker, wherein:
  i. a central-vision portion of said second display image that corresponds to a portion of the field of view of the second eye that includes said determined gaze direction, wherein the central-vision portion is either:
    unmodified compared to a corresponding portion in said base image; or
    modified so that visual characteristics of said central-vision portion of said second display image are changed compared to corresponding visual characteristics of a corresponding portion in said base image which modification improves the image quality of said central-vision portion relative to the corresponding portion in said base image, and
  ii. a non-central vision portion of said second display image that is different from said central-vision portion is either:
    unmodified compared to a corresponding portion in said base image; or
    modified so that visual characteristics of said noncentral vision portion of said second display image are changed compared to corresponding visual characteristics of a corresponding portion in said base image,
wherein as a result of said generating, an image quality of said non-central vision portion of said second display image is lower than the image quality of said central-vision portion of said second display image; and
to display said generated second display image on a display screen functionally associated with said computer processor so that the second eye of the person views said second display image on said display screen, wherein said non-central portion of said second display image is modified so that visual characteristics of said non-central vision portion of said second display image are changed compared to corresponding visual characteristics of a corresponding portion in said base image which modification degrades the image quality of said non-central vision portion relative to the corresponding portion in said base image, wherein said modification which degrades the image quality of said non-central vision portion relative to the corresponding portion in said base image includes at least reduced contrast.

19. The device of claim 15, said computer processor configured so that a size of a central-vision portion of a display image corresponds to a field of view of the first eye of at least about 1° and not more than about 20° that includes a determined gaze direction of the first eye.

20. The device of claim 15, said computer processor configured so that the central-vision portion of a display image is unmodified compared to a corresponding portion in a base image.

21. The device of claim 15, wherein said computer processor is configured to modify a base image so that visual characteristics of a central-vision portion of a generated display image are changed compared to corresponding visual characteristics of a corresponding portion in the base image which modification improves the image quality of the central-vision portion relative to the corresponding portion in the base image.

22. The device of claim 15, said computer processor configured so that a non-central vision portion of a display image completely surrounds said central-vision portion.

23. The device of claim 15, said computer processor configured so that a radial dimensions of a non-central vision portion of a display image corresponds to a field of view of a first eye of at least about 2°.

24. The device of claim 15, wherein:
said configuration of said computer processor to generate a display image comprises configuration also to generate a display image as an image data structure and
said configuration to display a generated display image comprises configuration to display an image data structure on said display screen.

25. The device of claim 15, wherein said configuration of said computer processor to generate and display a generated display image comprises:
configuration to generate a mask image that is non-dependent on the base image comprising a non-degrading central vision portion and a degrading non-central vision portion; and
configuration to display a generated mask image together with a base image on said display screen so as to concurrently generate and display a display image.

26. The device of claim 15, said computer processor configured to generate a display image also based on a provided display screen to first-eye cornea distance.

27. The device of claim 25, wherein as a result of said display of a generated mask image together with a base image the appearance of the central vision portion of the base image on said display screen is not effected so that the portions of the base image corresponding to the central-vision portion appear to a subject to be unmodified.

28. The device of claim 25, wherein as a result of said display of a generated mask image together with a base image the appearance of the non-central vision portion of the base image on the display screen is changed, so that the portions of the base image corresponding to the non-central vision portion appear to a subject to be degraded.

29. A method for image processing and display, comprising:
a. determining a gaze direction of a first eye of a person viewing an image on a display screen and providing said determined gaze direction to a computer processor;
b. subsequent to 'a', based on said determined gaze direction of the first eye, with a computer processor generating a display image for display to the first eye on said display screen from a received digital base image, wherein:
i. a central-vision portion of said display image that corresponds to a portion of the field of view of the first eye that includes said determined gaze direction is either:
unmodified compared to a corresponding portion in said base image; or
modified so that visual characteristics of said central-vision portion of said display image are changed compared to corresponding visual characteristics of a corresponding portion in said base image which modification improves the image quality of said central-vision portion relative to the corresponding portion in said base image, and
ii. a non-central vision portion of said display image that is different from said central-vision portion is either:
unmodified compared to a corresponding portion in said base image; or
modified so that visual characteristics of said noncentral vision portion of said display image are changed compared to corresponding visual characteristics of a corresponding portion in said base image,
wherein as a result of said generating, an image quality of said non-central vision portion of said display image is lower than the image quality of said central-vision portion of said display image; and
c. displaying said generated display image on said display screen so that the first eye of the person views said display image on said display screen,
wherein said non-central portion of said display image is modified so that visual characteristics of said non-central vision portion of said display image are changed compared to corresponding visual characteristics of a corresponding portion in said base image which modification degrades the image quality of said non-central vision portion relative to the corresponding portion in said base image, wherein said modification which degrades the image quality of said non-central vision portion relative to the corresponding portion in said base image includes at least one reduced contrast.

30. The method of claim 29, further comprising: displaying said generated display image on a display screen so that the second eye of the subject views said display image on a display screen.

* * * * *